(12) United States Patent
Bicalho

(10) Patent No.: US 12,263,211 B2
(45) Date of Patent: Apr. 1, 2025

(54) *KLEBSIELLA* VACCINE AND METHODS OF USE

(71) Applicant: Cornell University, Ithaca, NY (US)

(72) Inventor: Rodrigo Bicalho, Dryden, NY (US)

(73) Assignee: Cornell University, Ithaca, NY (US)

( * ) Notice: Subject to any disclaimer, the term of this patent is extended or adjusted under 35 U.S.C. 154(b) by 473 days.

(21) Appl. No.: 17/605,591

(22) PCT Filed: Apr. 27, 2020

(86) PCT No.: PCT/US2020/030038
§ 371 (c)(1),
(2) Date: Oct. 22, 2021

(87) PCT Pub. No.: WO2020/220014
PCT Pub. Date: Oct. 29, 2020

(65) Prior Publication Data
US 2022/0257743 A1    Aug. 18, 2022

Related U.S. Application Data

(60) Provisional application No. 62/979,795, filed on Feb. 21, 2020, provisional application No. 62/839,017, filed on Apr. 26, 2019.

(51) Int. Cl.
*A61K 39/02* (2006.01)
*A61K 39/108* (2006.01)
*A61P 31/04* (2006.01)
*C07K 14/245* (2006.01)
*C07K 14/255* (2006.01)
*C07K 14/26* (2006.01)
*A61K 39/00* (2006.01)

(52) U.S. Cl.
CPC .......... *A61K 39/0266* (2013.01); *A61P 31/04* (2018.01); *C07K 14/245* (2013.01); *C07K 14/255* (2013.01); *C07K 14/26* (2013.01); *A61K 2039/55594* (2013.01)

(58) Field of Classification Search
None
See application file for complete search history.

(56) References Cited

U.S. PATENT DOCUMENTS

| 6,610,836 B1 | 8/2003 | Breton et al. |
| 2016/0311894 A1 | 10/2016 | Chowdhury et al. |
| 2019/0070281 A1 | 3/2019 | Burkhardt et al. |

FOREIGN PATENT DOCUMENTS

RU    2209081 C1    7/2003

OTHER PUBLICATIONS

Whisstock et al., (Quarterly Reviews of Biophysics 2003, vol. 36 (3): 307-340,).*
NCBI, "DUF3748 domain-containing protein [Klebsiella pneumoniae]," NCBI, Reference Sequence: WP_015959175.1, Nov. 9, 2018.
McClelland et al., "Complete genome sequence of *Salmonella enterica* serovar Typhimurium LT2," Nature, Oct. 2001, pp. 852-856, vol. 413, No. 6858.
Database UniProt, "RecName: Full=DUF3748 domain-containing protein {ECO:0008006 | ProtNLM}," Uniprot: A6TFZ2, Aug. 21, 2007.
UniProtKB Accession No. A0A2X3GDW1, Protein of uncharacterized function (DUF3748), Sep. 12, 2018, 4 pages. www.uniprot.org/uniprot/A0A2X3GDW1.

* cited by examiner

*Primary Examiner* — Jennifer E Graser
(74) *Attorney, Agent, or Firm* — Hodgson Russ LLP

(57) ABSTRACT

Provided are compositions and methods that include a *K. pneumoniae* yidR protein or an antigenic segment of the protein, and homologs of the protein, and antigenic segments of the homologs. The compositions can be provided as vaccine formulations for use with humans and non-human animals, including but not limited to dairy cows. The compositions and methods are useful for prophylaxis and/or therapy of conditions associated with Gram negative bacteria that include *K. pneumonia, E. coli,* and other pathogenic Gram negative bacteria. The conditions include such bacterial infections generally, and include specifically mastitis and metritis. The compositions and methods can also improve fertility and milk production. Administration of the compositions can improve the likelihood of a first service conception.

14 Claims, 16 Drawing Sheets

Specification includes a Sequence Listing.

KLEBSIELLA VACCINE AND METHODS OF USE

CROSS REFERENCE TO RELATED APPLICATIONS

This application claims priority to U.S. provisional patent application No. 62/839,017, filed Apr. 26, 2019, and to U.S. provisional patent application No. 62/979,795, filed Feb. 21, 2020, the entire disclosures of each of which are incorporated herein by reference.

FIELD

The present disclosure relates to compositions and methods that are useful for protecting against infection by *Klebsiella* spp. and *Escherichia coli* in humans and a variety of non-human animals, and can inhibit mastitis, metritis, and improve milk production and reproduction function in certain mammals, such as dairy cows.

BACKGROUND

Bovine clinical mastitis (CM) is a highly prevalent and costly disease that is defined by an increase in milk somatic cell count (SCC) as a result of inflammation of the mammary gland, leading to abnormal milk and varying degrees of clinical severity[1]. This condition affects almost 25% of the 9.3 million dairy cows present in the United States every year (USDA, 2016), and negatively impacts animal welfare[2] and productivity[3,4]. It has been suggested that approximately 80% of all antimicrobials used on American dairy farms are for the treatment or prevention of mastitis[5]. Prevention strategies, improved management, and sanitation have reduced the number of contagious mastitis cases and have led to a change in the etiology of the disease in the last decade[6], making opportunistic environmental pathogens, including coliforms, major contributors to CM. Currently approximately 40% of all CM cases are associated with opportunistic Gram-negative bacteria; mainly *Klebsiella* spp. and *Escherichia coli*[7-9].

Studies have shown differences in the pathogenicity of *Klebsiella* spp. from other Gram-negative pathogens[10,11]. *Klebsiella* spp. causes longer intramammary infections than *E. coli*[12], more severe clinical episodes than *Serratia* spp and *E. coli*[13,14], and greater milk production loss and risk of culling than mastitis caused by *E. coli*[3,15]. Current guidelines do not recommend the use of intramammary antibiotics for cows diagnosed with Gram-negative mastitis[16,17].

In a recent randomized controlled field trial, our research team showed no improvement on clinical and bacterial outcomes and microbiome dynamics regarding treatment of mild and moderate coliform mastitis with a third generation cephalosporin in comparison to a no-treatment control[18].

There is accordingly an ongoing an unmet need for vaccine formulations that are suitable for broad use against *Klebsiella* infection, and in particular against *K. pneumonia*, for prophylaxis and therapy of mastitis, and a variety of other conditions correlated with the presence of Gram-negative bacteria. The present disclosure is pertinent to this need.

SUMMARY

The present disclosure provides a recombinant vaccine comprising a protein and derivatives of a protein described herein as the yidR protein. The disclosure includes methods of making the vaccine, and methods of using the vaccine. The vaccine is suitable for use in humans, and non-human mammals, and has functions that extend beyond immune protection. In particular, the present disclosure provides an analysis of the genomic structures, pangenomic profiles, virulence determinants, and resistomes of 308 *K. pneumoniae* isolates from human nosocomial infections and dairy cattle mastitis, including 96 newly sequenced mastitic-cow isolates. The disclosure includes a reverse vaccinology approach to identify protein-expressing for use as vaccine candidates. By in silico analysis, the disclosure reveals 10 genes that were present in all 308 isolates (human and bovine). Those genes were highly conserved at the DNA level, and we predicted them to have surface-associated antigens. The 10 vaccine candidate genes were cloned into *E. coli*-BL21, proteins were expressed, purified, adjuvanted with aluminum hydroxide, and evaluated as vaccines using a fatal murine *K. pneumoniae* peritonitis infection model. Only one recombinant protein (YidR) was able to rescue 92.3% of the mice from mortality. Based in part on this unexpected finding, a large randomized clinical trial was conducted and demonstrated that rYidR vaccination significantly decreased the incidence of *Klebsiella* spp. Surprisingly, cows in the rYidR group also had fewer cases of *E. coli* mastitis and affected cows had a dramatic decrease of disease severity when compared to the other groups. The rYidR vaccination also had a beneficial impact on metritis, mastitis, reproductive function, and milk production. Accordingly, the present disclosure provides in certain embodiments novel vaccines that can, among other purposes as described herein, aid the dairy industry in the control of *Klebsiella* spp. and *E. coli* mastitis. It is expected that the described vaccines will also be suitable for other animals that are susceptible to developing conditions associated with other conditions and other bacteria, including but not necessarily limited to swine (such as metritis, mastitis, and agalactia MMA-syndrome) and poultry (such as *Salmonella* spp. fecal shedding). Use of the described vaccines are also expected to have beneficial effects in humans, and other non-human animals.

Thus, in embodiments, the disclosure provides a YidR protein or antigenic fragment thereof. In embodiments, the protein comprises the amino acid sequence of SEQ ID NO:2, or an amino acid sequence having from 79.0-99.9% identity to SEQ ID NO:2, or an antigenic fragment thereof, the protein or the antigenic fragment thereof optionally comprising a purification tag. Compositions comprising such proteins and/or antigenic fragments of them are included, and may be provided as vaccines, e.g., vaccine formulations, which may comprise an adjuvant. Expression vectors encoding the proteins or antigenic fragments thereof are included. A plurality of cells comprising such an expression vector are included. The disclosure also includes making proteins and antigenic segments of the proteins by expressing the proteins or such segments from an expression vector in a plurality of cells in vitro, and optionally separating the protein or the antigenic fragment thereof from the plurality of cells. Purified proteins and antigenic segments of the proteins are included.

The disclosure includes methods comprising administering to an individual in need thereof a composition of the disclosure. In embodiments, the composition is administered to some or all members of a population. In embodiments, the individual is in need of prophylaxis or treatment of a condition associated with the presence of Gram negative pathogenic bacteria. In embodiments, the Gram negative pathogenic bacteria comprise *Klebsiella, E. coli, Salmo-* nella, or a combination thereof. In embodiments, the individual in need of the composition is a bovine mammal, including but not limited to a female bovine mammal. In embodiments, the female bovine mammal is in need of the composition for prophylaxis or therapy of mastitis or metritis. In embodiments, administration of a composition to an individual inhibits the development or reduces the severity of mastitis. The mastitis may be associated with any Gram negative bacteria, including but not limited to *Klebsiella* and *E. coli*. In embodiments, administration of a described composition inhibits the development or reduces the severity of metritis. In embodiments, the metritis may be associated with any Gram negative bacteria, including but not limited to *Klebsiella* and *E. coli*. In embodiments, administering a described composition improves the likelihood of a first service conception, including but not limited to first service conception in one or more female bovine mammal, which include but are not limited to primaparous and multiparous bovines. In embodiments, administering a described improves milk production by the female bovine mammal, such as by increasing milk production.

In embodiments, the disclosure provides an article of manufacture comprising at least one container comprising a described composition. The article of manufacture may further comprise printed material describing an indication for the use of the composition. The article of manufacture may further comprising a device for administering the composition, such as a syringe and/or a needle, which may be suitable for intravenous or subcutaneous administration.

DETAILED DESCRIPTION

Figure 1:
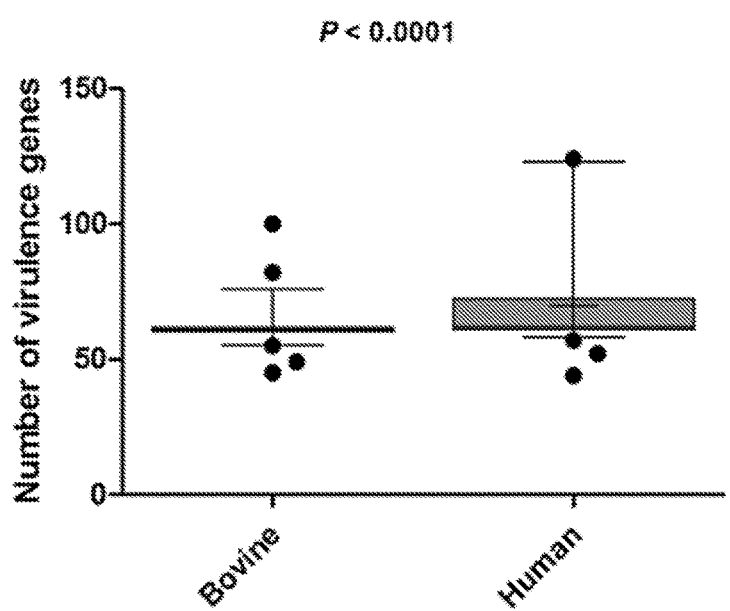
FIG. 1: Virulence genes in 308 *K. pneumoniae* isolates. (A) Number of virulence genes per isolate. (B) Distribution of virulence genes in 123 bovine isolates and 185 human isolates. Each number indicates the number of different virulence genes found within each group. (C) Frequency of gene clusters among 123 bovine isolates and 185 human isolates. For each pair of bars of each system or gene, the upper bar represents bovine isolates and the lower bar represents human isolates. (D) Distribution of virulence genes in newly sequenced clinical *K. pneumoniae* isolates. (E) Distribution of virulence genes in 123 bovine isolates.
Figure 1:
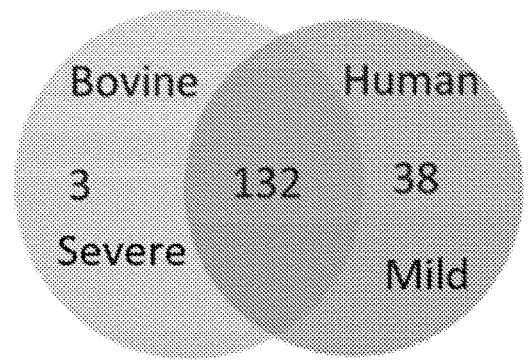
Figure 1:
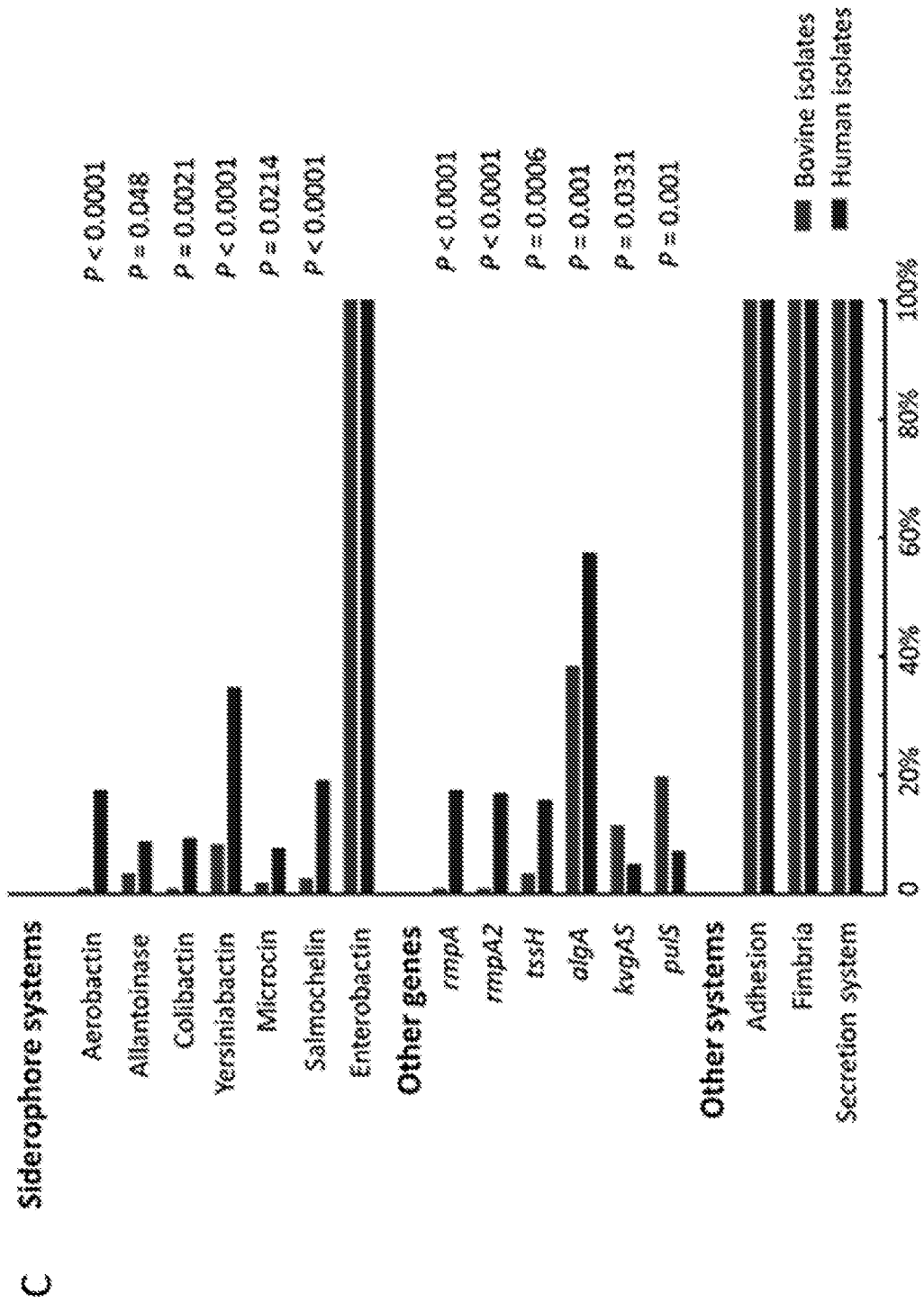
Figure 1:
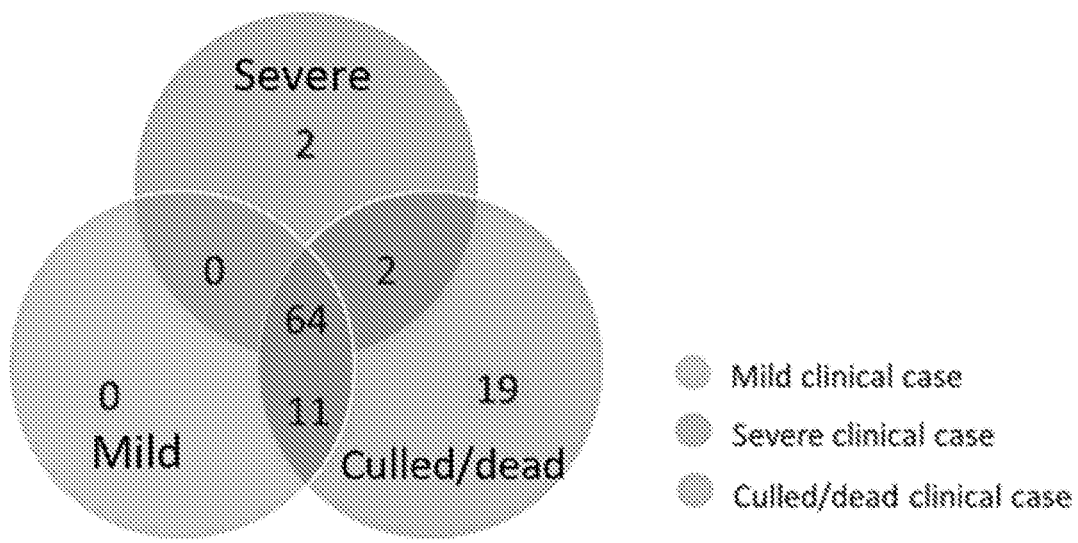
Figure 1:
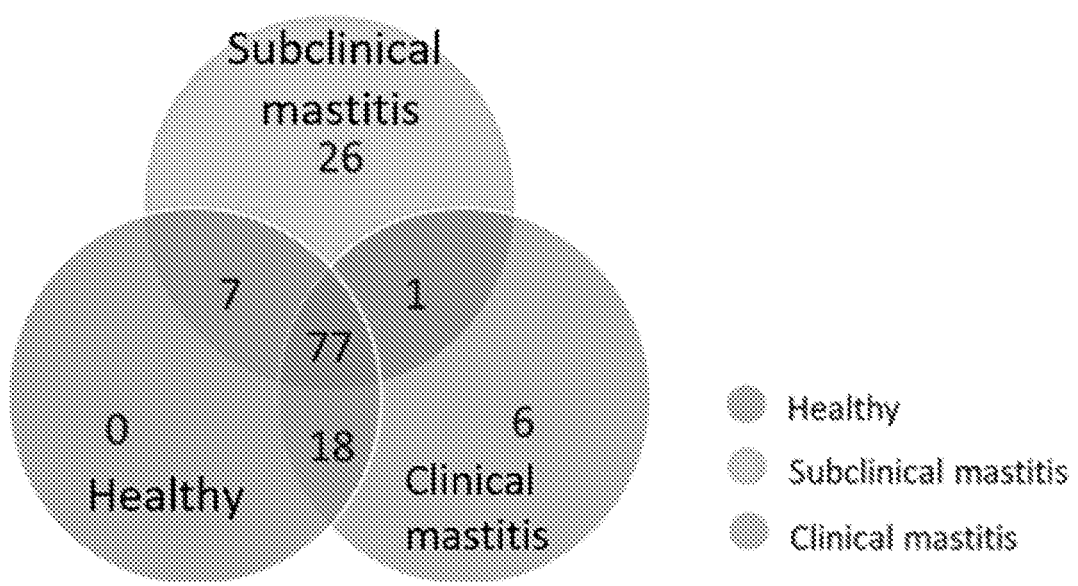

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Every numerical range given throughout this specification includes its upper and lower values, as well as every narrower numerical range that falls within it, as if such narrower numerical ranges were all expressly written herein.

The disclosure includes all polynucleotide sequences described herein, the DNA and RNA equivalents of all such polynucleotides, including but not limited to cDNA constructs, and all polypeptides encoded by the polynucleotides described herein.

In embodiments, the disclosure provides a vaccine formulation that comprises at least one protein component. In an embodiment, the protein component is a *K. pneumoniae* yidR protein or an antigenic segment of the protein. In embodiments, an antigenic fragment, e.g., a segment, comprises 8-408 amino acids, including all integers and ranges of integers there between, of SEQ ID NO:2, or a sequence that is at least 79.0% identical to such a sequence. In embodiments, the antigenic fragment comprises 8-20 amino acids, 8-15 amino acids, 8-12 amino acids, 8-10 amino acids, or at least 8, 9, 10, 11, 12, 13, 14, 15, 16, 17, 18, 19, or 20 contiguous amino acids, from the full-length protein. In embodiments, the protein component is a YidR protein derivative, which is a highly conserved protein amongst several Gram-negative bacteria. In one embodiment, the protein component is a polypeptide encoded by the nucleotide sequence:

(SEQ ID NO: 1)
ATGAAACAAGTCACTTTTGCTCCCCGTCATCACCAGCTTACCAATATTA

ATACCTGGACTCCCGACAGCCAGTGGCTGGTATTCGACGTTCGTCCGTC

CGGCGCATCGTTTACCGGCGAAACCATTGAGCGAGTGAACGTAAACAGC

GGTACTGTGGAGACCATTTATCGTGCCACGCAGGGCGCGCACGTGGGCG

TGGTAACCGTGCATCCAACCCAGGAGCGCTATGTGTTTATTCATGGCCC

-continued

```
CGAGCGGCCGGATGCGCAGTGGCAGTATGATTTTCATCATCGCCGCGGG

GTGGTGGCCTTTCAGGGGGCTGTCGAGAATCTGGACGCCATGGACATTA

CCCCCCCCTACACGCCCGGCGCGCTGCGCGGCGGCAGCCACGTCCATGT

CTATAGCCCCAACGGTCAGTTTGTCAGTTTTACCTACAACGATCACGTG

CTGCACCAGCGCGATCCGGCGCTGGATCTGCGCAACGTCGGCGTGGCGG

CGCCCTATGGACCGGTGACGCCGCAGGGACAGCATCCGCGCGAATATGG

CGGCAGCCACTGGTGTGTGCTGGTAAGCCGCACGACGCCGGCACCCGCG

CCGGGCAGCGATGAGATTAATCGCGCCTATGAGGAGGGCTGGGTCGGGA

ACCATACTCTGGCGTTTATTGGCGATACGCTGGCGGAAAATGGCGATAA

AGTGCCTGAGCTGTTTATTGTCGATCTGCCGCAGGATGAAGCCGGCTGG

AAGCAGCCTGGCGGGGCGCCGCTGGCCGGTACCGCAACCACAATGCCGG

CGCCGCCGGCGGGCGTCAGCCAGCGTCGTTTGACCTTCACCCACCATCG

CCGCTACCCGGGACTGGTGAACGTCCCGCGCCACTGGGTGCGCGCCAAT

CCCCAGGCGACGGCGATAGCCTTTCTGATGCGCGACGACGCCGGCGTAG

TGCAGCTGTGGCTTATTTCCCCGCAGGGGGCGAGCCGCGGCAGTTGAC

GCATCACGCGTCGGGTATCCAGTCGGCGTTTAACTGGCATCCGTCGGGA

GAGTGGCTGGGTTTTGCGCTGGAGGATCGGATTGCCTGCTGCCATGCCG

GTACGGGAGATATCACCTTTTTAACCGATACGCATGCGCATGCGCCCTC

GGCGGACGCGATCGTCTTTTCGCCAGACGGTAAACAGATTGCCTGGATG

GAGGAGGTGGACGGTTATCGTCAGCTGTGGGTTACGCAGACCGGACGAT

AA.
```

In embodiments, the protein is a polypeptide that is from 79.0-99.0%, inclusive, and including all numbers there between to the first decimal point, similar to the protein encoded by SEQ ID NO:1, or a contiguous segment of such a protein that comprises conserved domains that are associated with Tol-dependent translocation of colicins into *E. coli*, which will be recognized by those skilled in the art. In embodiments, similarity is measured without including the sequence of a tag, such as a purification tag.

The amino acid sequence encoded by SEQ ID NO:1 is:

(SEQ ID NO: 2)
MKQVTFAPRHHQLTNINTWTPDSQWLVFDVRPSGASFTGETIERVNVNS

GTVETIYRATQGAHVGVVTVHPTQERYVFIHGPERPDAQWQYDFHHRRG

VVAFQGAVENLDAMDITPPYTPGALRGGSHVHVYSPNGQFVSFTYNDHV

LHQRDPALDLRNVGVAAPYGPVTPQGQHPREYGGSHWCVLVSRTTPAPA

PGSDEINRAYEEGWVGNHTLAFIGDTLAENGDKVPELFIVDLPQDEAGW

KQPGGAPLAGTATTMPAPPAGVSQRRLTFTHHRRYPGLVNVPRHWVRAN

PQATAIAFLMRDDAGVVQLWLISPQGGEPRQLTHHASGIQSAFNWHPSG

EWLGFALEDRIACCHAGTGDITFLTDTHAHAPSADAIVFSPDGKQIAWM

EEVDGYRQLWVTQTGR

In embodiments, the disclosure provides for reducing infection by bacteria, including but not limited to *Klebsiella* bacteria, including but not necessarily limited to *K. pneumoniae*. In embodiments, administering a vaccine of this disclosure also stimulates a therapeutic and/or prophylactic effect against non-*Klebsiella* bacteria and/or conditions associated with the presence of such bacteria, such as mastitis that is associated with the presence of Gram-negative bacteria, including but not necessarily limited to *E. coli*. Thus, in embodiments, the presently provided compositions and methods are suitable for prophylaxis and/or therapy of mastitis caused in whole or part by Gram-negative bacteria.

In embodiments, performance of a method of the disclosure results in one or a combination of the following results:
1) improved health of the animal, such as increased conception rate at first service;
2) prophylaxis and/or therapy of mastitis, which may include reducing the severity of clinical signs of mastitis, and/or reducing the duration of mastitis;
3) prophylaxis and/or therapy of metritis;
4) increased fertility of animals, a non-limiting example of which comprises improving the incidence of conception at first service;
5) increased milk production; and
6) reduced mortality due to bacterial infection.

In embodiments, proteins encompassed by the disclosure and segments thereof include YidR protein from *E. coli* 0157:H7, the protein comprising the following amino acid sequence:

(SEQ ID NO: 3)
MAGPVLYQDRAMKQITEAPRNHLLTNTNTWTPDSQWLVFDVRPSGASFT

GETIERVNIHTGEVEVIYRASQGAHVGVVTVHPKSEKYVFIHGPENPDE

TWHYDFHHRRGVIVEGGKMSNLDAMDITAPYTPGVLRGGSHVHVFSPNG

ERVSFTYNDHVMHELDPALDLRNVGVAAPFGPVNVQKQHPREYSGSHWC

VLVSKTTPTPQPGSDEINRAYEEGWVGNHALAFIGDTLSPKGEKVPELF

IVELPQDEAGWKAAGDAPLSGTETTLPAPPRGVVQRRLTFTHHRAYPGL

VNVPRHWVRCNPQGTQIAFLMRDDNGIVQLWLISPQGGEPRQLTHNKTD

IQSAFNWHPSGEWLGEVLDNRIACAHAQSGEVEYLTEHHANSPSADAVV

ESPDGQWLAWMEGGQLWITETDR.

In embodiments, proteins encompassed by the disclosure and antigenic segments thereof include YidR protein from *Salmonella enterica*, the protein comprising the following amino acid sequence:

(SEQ ID NO: 4)
MKQITFTPRHHQLTNTNTWTPDSQWLVFDVRPSGASFTGKTIERVNVHT

GDVEVIYRAVQGAHVGVVTVHPADNHYVFIHGPENPDETWHYDFHHRRG

VIATPGGVTNLDAMDITAPYTPGALRGGSHVHVFSPNGELVSFTYNDHV

LHERDPALDLRNVGVAAPYGPVTVPVQHPREYSGSHWCVLVSRTTPAPR

PGSDDINRAYEEGWVGNRQIAFIGDTLSLTGQKVPELFIVDLPCHENGW

KQAGDTPLTGTESTMPSPPLGVVQRRLTFTHQRVYPGLTNEPRHWVRSN

PQATAIAFLMRDDNGVAQLWLISPQGGEPRQLTHHATGVQSAFNWHPSG

KWLGLVLENRIACCDAQSGRIDFLTARHDNPPSADAVVFSPDGRHVAWM

EEVKGFRQLWVTETGR.

In embodiments, the disclosure provides isolated or recombinantly produced polypeptides for use as vaccines, as further described herein. In embodiments, the polypeptide comprises a sequence that is 79.0% to 99.9% identical to the sequence of any protein sequence described herein. In embodiments, said identity is with respect to SEQ ID NO:2, or to an antigenic segment of fragment thereof, or to SEQ ID NO:3, or to an antigenic segment or fragment thereof, or the SEQ ID NO:4, or to an antigenic segment or fragment thereof. Antigenic segments are those predicted to be able to elicit an immune response, including but not limited to stimulation of antibodies that recognize the antigenic segments, and accordingly will recognize the intact protein. Antigenic segments are therefore immunogenic. It is expected that inclusion of antigenic segments in a protein vaccine can increase efficacy of the protein vaccine. In embodiments, antigenic segments of proteins of this disclosure are summarized in Table 2.

To determine the percent identity of two amino acid sequences, the sequences are aligned and amino acids at corresponding positions are then compared. When a position in the first sequence is occupied by the same amino acid as the corresponding position in the second sequence, then the polypeptides are identical at that position. The percent identity between the two sequences is a function of the number of identical positions shared by the sequences (i.e., % identity=# of identical positions/total # of positions×100). In embodiments, at least one amino acid is substituted for another amino acid, or one or more amino acids are deleted. Amino acid insertions are also included. Substitution mutations can be made to change an amino acid in the resulting protein in a non-conservative or in a conservative manner. The disclosure includes sequences containing conservative changes which do not decrease the efficacy of a vaccine prepared from the resulting protein. Thus, amino acid changes can be made to replace or substitute one or more, one or a few, one or several, one to five, one to ten, or such other number of amino acids in the sequence protein provided herein to generate mutants or variants thereof.

In embodiments, a bacterial protein or immunogenic fragment thereof may be provided as a segment of a fusion protein, e.g., a contiguous polypeptide comprising distinct segments that originate from at least two distinct polypeptides. For example, the fusion protein may comprise a bacterial protein or derivative thereof and a segment that functions to increase favorable pharmacokinetic properties. In embodiments, a polypeptide described herein may be provided as a fusion protein with an immunoglobulin protein. In embodiments, the fusion protein comprises at least one Ig fragment crystallizable region (Fc region). In some implementations the Fc region can be of any Ig isotype. In embodiments, the Ig component comprises an IgG Fc region that is an $IgG_1$, $IgG_2$, $IgG_3$, or $IgG_4$ isotype.

In embodiments, the protein of SEQ ID NO:2 or an immunogenic fragment thereof may include additional amino acids, such as a purification tag. In an embodiment, the purification tag comprises a series of Histidines. As in known in the art, the number of Histidines in a His-tag can be variable. In an embodiment, a His-tag is a linear sequence of n histidine residues where n is typically 6-10. His-tags achieve purification by binding specifically to nickel or cobalt ions, which may be for example, attached to a substrate, such as any suitable beads. The His-tag, or any other suitable purification tag, may be placed at the N-terminus of the protein, at the C-terminus of the protein, or interior to the protein. In embodiments, a FLAG-tag, or FLAG octapeptide, or FLAG epitope, may be included in proteins of this disclosure. Suitable FLAG sequences are known in the art. In embodiments, a Small Ubiquitin-related MOdifier (SUMO) tag, such as a His-SUMO tag can be included. In embodiments, amino acid sequences corresponding to protease cleavage sites can be included, such as for protein identification, separation, purification, etc. In embodiments, the protease cleavage sites can be included between the purification tag and the protein of SEQ ID NO:2 or between the purification tag and the immunogenic fragment thereof. The proteins can be purified to any desired degree of purity.

In embodiments, the disclosure is effective in providing a prophylactic effect against one or more types of *Klebsiella* or other types of bacteria that are resistant to one or more antibiotics. In embodiments, the disclosure provides for inhibiting formation of biofilms that contain the described bacteria.

In various embodiments, a vaccine of this disclosure can be used with any suitable antibiotics, examples of which include but are not limited to members of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, etc.

Vaccine formulations used in the methods of this disclosure can be provided in a variety of forms and delivered via a variety of routes. Compositions for use in humans or non-human mammals can be prepared by mixing the vaccine protein component(s) with any suitable pharmaceutically acceptable carriers, excipients and/or stabilizers. Some examples of compositions suitable for mixing with a vaccine protein as described herein can be found in: Remington: The Science and Practice of Pharmacy (2005) 21st Edition, Philadelphia, PA Lippincott Williams & Wilkins. Vaccine formulations may also comprise one or more suitable adjuvants. In embodiments, the adjuvant comprises aluminum. In embodiments, the adjuvant is selected from aluminum hydroxide, aluminum phosphate, alum (potassium aluminum sulfate), and mixed aluminum salts. In embodiments, the adjuvant comprises onophosphoryl lipid A (MPL). In embodiments, the adjuvant comprises an oil-in-water emulsion. Additional and non-limiting examples of components which may have adjuvant function include liposomes and archaeosomes, calcium salts, nanoparticles and microparticles, saponins, immune-stimulating complexes, nonionic block copolymers, derivatized polysaccharides, carrier proteins, other bacterial products and their derivatives, cytokines, and complement derivatives. In certain embodiments, the method can be performed prior to, concurrently, or subsequent to conventional anti-bacterial and anti-inflammatory approaches, including but not limited to antibiotic regimens. In an embodiment, IL-8 is also administered to the animal.

In embodiments, the protein component is provided in a dispersion or other formulation that renders the vaccine more potent than, for example, a reference composition.

Dosing of the vaccines, e.g., the amount of the protein component and any other active ingredients, can be determined based on various factors known to those skilled in the art, which include but are not limited to the age, size, gender, and type of animal to which the vaccine is administered. In embodiments, the vaccine is administered to a human or non-human animal that is at risk for infection, or is already infected, with *Klebsiella*, *E. coli*, or *Salmonella*.

In embodiments, a described vaccine is administered to a female mammal, including but not necessarily limited to one or a plurality of dairy cows. In embodiments, the vaccine is administered before, during, or after pregnancy. The vaccine may be administered to a female mammal who has never been pregnant, has only been pregnant once, or has been pregnant more than once. Thus, vaccinations may be given to nulliparous, primaparous and multiparous female mammals, or only to one of these types of female mammals. Pre-partum and postpartum vaccinations are included. In embodiments, the composition is administered to a female mammal that has recently given birth, and thus a postpartum administration is used. In one non-limiting example, a postpartum administration of a described vaccine is administered to a mammal, such as a dairy cow, within 72 hours of giving birth (parturition). Administering within shorter or longer times after parturition is also encompassed by this disclosure. In certain non-limiting examples, the described vaccine is administered immediately post partition, and up to 20 weeks after parturition. In certain approaches the disclosure thus includes administering on the same day as parturition, or within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140 days, inclusive, and including all ranges of integers there between. In embodiments, a composition is administered before parturition and after parturition. In embodiments, the post-parturition period may be defined by a period of days in milk, such a period encompassing from 1-140 days in milk, inclusive, and include all numbers and intervals there between. In embodiments, the vaccine is administered during a gestation period. The disclosure includes administering at least one dose, and administering 2, 3, 4, 5, or more doses during any particular time period to the same animal. Polynucleotide vaccines, such as DNA vaccines, and any suitable expression vector and/or viral construct that encodes a polypeptide described herein are also included and can be used in methods of this disclosure.

In embodiments, a protein component of this disclosure is modified relative to its naturally occurring form. In embodiments, the protein comprises a tag, such as a purification tag, one non-limiting embodiment of which includes a histidine tag. The protein component may also comprise other features, such as an introduced protease cleavage site. In embodiments, a protein described herein is combined with one or more solutions, buffers, emulsions, etc., that are pharmaceutically acceptable and enhance one or more immunogenic properties of the protein component, relative to the protein component alone, or relative to the protein component in a control formulation, such as a saline solution. Further, the vaccine may be provided in a tablet, liquid, powder, etc., and may include a controlled release composition, or other agents to influence its immunogenicity, bio-availability, etc. Notwithstanding the foregoing description, in embodiments, a vaccine of this disclosure comprises a cell-free vaccine. In embodiments, a vaccine of this disclosure is free from any bacterial extract that comprises bacterial components that are not the YidR protein, and may be from any type of bacterins, siderophore receptors, and porins. In embodiments, the described YidR protein is the only protein component in the composition. In embodiments, the described YidR protein, and optionally an adjuvant and other components that do not have biological activity (such as pharmaceutically acceptable additives), are the only biologically active components in the composition. Thus, the disclosure includes the proviso that any component described herein, except for the YidR protein, may be excluded from the compositions and methods of the disclosure.

Protein components of vaccines described herein may be produced recombinantly, and as such the disclosure includes expression vectors and recombinant polynucleotides encoding the protein component. The disclosure also comprises expressing the protein component recombinantly in a cell culture, and separating the protein from the cell culture. The protein may be purified using standard approaches to any desired degree of purity. Kits comprising expression vectors encoding the protein component of the vaccines of this disclosure are also provided.

A vaccine described herein can be administered to an individual using any available method and route, including oral, parenteral, subcutaneous, intraperitoneal, intrapulmonary, and intranasal administrations. Parenteral infusions include intramuscular, intravenous, intra-arterial, intraperitoneal, intravaginal, intrauterine, and subcutaneous administration. In embodiments, the vaccine is added to feed, and/or drinking water. In embodiments, the vaccine formulations are used in prophylactic or therapeutic approaches.

It is expected that methods of the present disclosure will be applicable to any animal that is susceptible to *Klebsiella* infection, and/or to developing Gram-negative mastitis, or is otherwise in need of or would benefit from receiving a composition of this disclosure.

In embodiments, the disclosure is directed to humans. In embodiments, the vaccine is administered to any human individual in need thereof. In embodiments, the human is an adult, an adolescent, a child, or an infant. In embodiments, the human is an immunocompromised individual. In embodiments, the individual has a bacterial infection of blood. In embodiments, the individual is at risk for developing or has developed sepsis. In embodiments, the individual has a bacterial infection of a wound or surgical site. In embodiments, the individual has or is at risk for developing meningitis. In embodiments, the individual is at risk of contracting or has a nosocomial *Klebsiella* infection. In embodiments, the individual is intubated, and/or is on a ventilator. In embodiments, the individual has any catheter, including but not limited to a vein catheter and a Foley catheter. In embodiments, the human is female human and is pregnant, or has recently given birth.

In embodiments, the disclosure includes veterinary approaches, and thus in this aspect pertains to non-human mammals. In embodiments, the non-human female mammal to which the vaccine is administered is a ruminant, including but not necessarily limited to bovines, sheep, antelopes, deer, giraffes, and their relatives, and further can include pseudoruminants, such as the camelids. In embodiments, the ruminant is a female bovine mammal that is a member of the genus Bos, such as oxen, cows, and buffalo. In one embodiment the ruminant is a dairy cow. In embodiments, the female mammal is an ungulate.

In an embodiment the disclosure includes a vaccine of this disclosure administered to a member of the genus Sus, and therefore encompasses practicing the invention with any swine, examples of which are not limited to the domestic pig (i.e., *Sus domesticus*), also commonly referred to as a swine or a hog. The disclosure also includes administering the vaccines to non-bovine and non-ruminant mammals, including but not necessarily limited to equines, canines, and felines. Any type of equines, canines and felines are included. In embodiments, the felines are domesticated cats.

In embodiments, the felines are so-called big cats, which include lions, tigers, leopards, and cougars. Felines also include but are not limited to cheetahs, lynx, jaguars, panthers and civets.

In embodiments, compositions of this disclosure are administered to avian animals. In embodiments, the avian animals are any type of poultry. In embodiments, the avian animals are *Galliformes* and thus include any members of the order of heavy-bodied ground-feeding birds that includes turkey, grouse, chicken, New World quail and Old World quail. In embodiments, the avian animals are domesticated fowl, including but not limited to domesticated chickens and turkeys. In embodiments, the chickens are *Gallus gallus*, such as *Gallus gallus domesticus*. In embodiments, the chickens are roosters or hens. In embodiments, the chickens are broiler chickens. In embodiments, the avian animals are adults, juveniles, or embryos. In an embodiment, a composition of this disclosure is applied to eggs. In embodiments, vaccines of this disclosure administered to a population of avian animals, i.e., a flock. In embodiments, from 50-85% or more members of the flock are vaccinated to achieve, for example, herd or flock immunity; thus this approach applies to a plurality of mammals as well. In particular, in embodiments, populations or sub-populations of animals are vaccinated to promote herd immunity, and/or to promote improved health in members of the population. In embodiments, the disclosure provides for more a more efficient/effective immunization relative previously available compositions and methods.

In embodiments, the disclosure provides an article of manufacture comprising packaging and at least one sealed container. The sealed container can comprise a described protein that is suitable for reconstitution into a vaccine formulation, or the container can comprise a ready to use vaccine formulation. The vaccine formulation comprises an effective amount of the described protein. The packaging comprises printed material providing an indication that the vaccine is for administration to any animal described herein, and/or can include a description of the route of administration, dosage, and an indication of the condition to be addressed using the vaccine.

The bacteria against which the presently provided vaccines may be used can be present on or within an animal, such as a human or non-human mammal, and may be confined to a particular location, tissue or organ. In embodiments, the disclosure provides a prophylactic effect against persister cells and/or dormant viable but non-culturable (VBNC) cells.

In embodiments, an "effective amount" of the vaccine is used. An effective amount is that amount of the vaccine which is sufficient to provide a beneficial effect to the subject to which the vaccine is administered. In embodiments, an effective amount of a vaccine comprises a per/animal dose of 0.01 mg to 100 mg of a described protein or antigenic segment thereof, inclusive, and including all numbers and ranges of numbers there between to the second decimal point. In embodiments, an effective amount of the protein or antigenic segment thereof comprises 0.1 mg. 0.2 mg, 0.3 mg, 0.4 mg, 0.5 mg, 0.6 mg, 0.7 mg, 0.8 mg, 0.9 mg, 1.0 mg, or more. In embodiments, an effective amount of the protein or antigenic segment thereof comprises at least 0.01 mg, or at least any of the foregoing values.

In embodiments, vaccination with a composition described herein elicits a humoral immune response, or a cell-mediated immune response, or both. In embodiments, antibodies that recognize at least one epitope expressed by the described bacteria are produced. In embodiments, neutralizing antibodies may be produced. In embodiments, vaccination results in complete or partial protection against exposure to pathogenic Gram-negative bacteria that can include but is not necessarily limited to one or a combination of *Klebsiella, E. coli*, and *Salmonella*. In embodiments, vaccination according to this disclosure reduces or prevents one or more symptoms of *Klebsiella, E. coli*, or *Salmonella* infection. In an embodiment, vaccination prevents *Klebsiella, E. coli*, or *Salmonella* infection, e.g., the vaccination inhibits the development or prevents infection by any of *Klebsiella pneumoniae, Klebsiella oxytoca, Klebsiella variicola, Klebsiella aerogenes, Klebsiella granulomatis, Klebsiella michiganensis, Klebsiella quasipneumoniae, Klebsiella grimontii, Klebsiella planticola, Salmonella enterica,* and *Salmonella bongori*. In embodiments, administration of a protein as described herein is more effective at producing one or more of the described results than a reference. The reference may be any suitable reference, and may include a previously determined value. The reference may be administration of a different protein, or the same protein but in a different amount, a different composition that contains the protein, and/or via a different route. In embodiments, a reference value comprises vaccination with J-5 bacterin as further described below, and/or vaccination with a vaccine sold under the trade name KLEBvax™. In embodiments, administration of a presently provided vaccine exhibits, relative to a reference, decreased mortality rates (death and culling) and/or reducing milk production losses, including but not limited to animals diagnosed with *E. coli* mastitis, and/or improving the chance of conception at first service. In embodiments, a described vaccine is administered only a single time, or is administered more than one time, including 2, 3, 4, 5, or more times, depending on the type of animal and the particular condition that is being addressed.

With respect to the presently provided compositions and methods, vaccines using core cell wall antigens have been previously developed to provide protection against a variety of Gram-negative pathogens and have been registered for the reduction of severity in mastitis caused by the coliform organisms[19-21]. The severity of clinical symptoms of coliform mastitis has been shown to be reduced by immunization with commercially available J-5 bacterin[19]. The efficacy of this vaccine for the prevention of mastitis caused by *E. coli* has been investigated in experimental challenge studies[19,21-24]. All these studies implied that immunization with J-5 bacterin reduced the severity of local and systemic signs of CM following intramammary challenge with *E. coli*. Vaccination with the J-5 bacterin has been reported in some early studies to reduce the incidence of naturally occurring clinical coliform mastitis during early lactation[23]. However, in subsequent field studies, J-5 vaccination was associated with reduction in culling due to CM, but not with the reduction in the incidence of clinical coliform mastitis[22, 25,26]. Currently, it is generally accepted that J-5 vaccination lessens clinical signs of disease but does not decrease the incidence of *E. coli* and/or *Klebsiella* spp. mastitis[27].

In more detail, the first vaccine registered by the USDA for the prevention of *Klebsiella* spp. mastitis became commercially available in the United States (KLEBvax™ SRP®, Epitopix, Willmar, MN). KLEBvax™ is a commercially available, USDA registered, *Klebsiella pneumoniae* bacterial extract (Siderophore Receptors and Porins) vaccine. Gorden et al. (2018), reported that prepartum vaccination with KLEBvax™ significantly reduced CM by *Klebsiella* spp. but postpartum vaccination did not reduce the incidence of *Klebsiella* CM[28]. However, in a randomized clinical trial of the present disclosure and as described further in the Examples below, a total of 3,107 cows were allocated into 1 of three treatment groups; 1,045 cows were allocated to receive a placebo injection, 1,036 cows were immunized with rYidR protein, and 1,026 cows were immunized with KLEBvax™ SRP® (Epitopix, Willmar, MN). All vaccines and placebo treatments were administered twice during the prepartum period; the first injection at 220 days of gestation and the second at 241 days of gestation. KLEBvax™ did not decrease the incidence of *Klebsiella* spp. nor the severity of the Gram-negative mastitis cases. Thus, advantages of the vaccines of the present disclosure will be apparent to those skilled in the art, when given the benefit of the present examples and figures.

The following Examples are intended to illustrate various embodiments of the disclosure, but are not intended to be limiting.

Example 1

Genomic Diversity, Virulence, and Antimicrobial Resistance of *Klebsiella pneumoniae* Strains from Cows and Humans.

We assembled a collection of *K. pneumoniae* strains recovered from 143 mastitic cows with various degrees of disease severity and sequenced the genomes of 96 distinct isolates to compare their genomic structures, virulence factors, and antimicrobial resistance (AMR) genes with those of the *K. pneumoniae* isolates studied by Holt et al.[29]. We investigated the pangenomic gene functions of 308 isolates in total and identified a group of virulence genes that had a different distribution between *K. pneumoniae* isolates collected from dairy cows and humans. Furthermore, we found a resistance plasmid not previously identified in the United States and clarified its genetic context according to the closed plasmid structure.

Example 2

Diversity and Antimicrobial Resistance Profile of *K. pneumoniae* on Dairy Farms.

We isolated 143 non-replicate *K. pneumoniae* strains from mastitic dairy cows from four farms located in upstate New York state, USA. Molecular typing of the isolates using pulsed-field gel electrophoresis (PFGE) identified 97 distinct PFGE groups, revealing a high genetic diversity within the isolate collection. Capsule locus typing of those 143 isolates showed that 127 (88.8%) were assigned to 44 known capsule loci. The capsule loci KN3 (30/143, 21%), K13 (15/143, 11%), and KN1 (10/143, 7%) were the most prevalent in our sample set, accounting for approximately 39% of all infections. High genetic diversity was also reflected by the sequence types (STs) of those strains. Among the 96 newly sequenced strains, 46 possessed new alleles of the housekeeping genes used for multilocus sequence typing (MLST), and no predominant STs were found. These new alleles were assigned 43 new STs. Overall, the AMR profiles were diverse among these strains, and 40% (57/143) were resistant to one or more antimicrobial agents. The agent to which the highest prevalence of resistance was detected was streptomycin (29.4%, 42/143), followed by tetracycline (5.6%, 8/143) and gentamicin (4.2%, 6/143). Using the genomic data for the 96 newly sequenced isolates from mastitic cows, we detected 17 AMR genes with varying prevalence. The fosA (fosfomycin resistance), oqxAB (quinolones resistance), blaAmpH (β-lactamase), and blaSHV (β-lactamase) genes were common resistance genes found in our isolate collection. The resistance to streptomycin in our isolate collection was attributed to the strA and strB genes, located on an IncHI1B-type plasmid in 27 of the 96 strains. Analysis of the genetic environment revealed that the strA and strB genes were flanked by transposon Tn5393, the most common mobile element that mediates the transmission of strAB genes across species.

Example 3

Identification of an IncN-Type Plasmid Carrying $bla_{CTX-M-1}$ and mph(A).

We found that four isolates were resistant to ceftiofur. Among those, three strains that had genomic sequences were found to coharbor the $bla_{CTX-M-1}$ (β-lactamase) and mph(A) (macrolide resistance). Comparison of the sequences by BLASTn analysis showed that all three contigs shared a high degree of similarity with the sequence of pL2-43 (GenBank accession no. KJ484641), an IncN-type plasmid found in an *E. coli* isolate recovered from a lamb in Switzerland in 2014[30]. Analysis of the plasmid sequences confirmed that they carried the same plasmid (named pC5) that coharbored the $bla_{CTX-M-1}$ and mph(A) genes. The complete sequence of pC5 (GenBank accession no. MF953243) is 41,608 bp in size and carries 51 open reading frames (ORFs).

Example 4

Extensive Diversity of Virulence Genes Among Bovine and Human Isolates.

In total, we detected 173 virulence genes in the 308 isolates. These included 135 and 170 virulence genes found in the bovine and human isolates, respectively, of which 132 genes were common to both types of isolates (FIG. 1). The enterobactin loci, adhesion-related gene clusters, secretion system-related gene clusters, and fimbria gene clusters were found in all isolates. We then investigated the functions of all genes across the 308 human and bovine isolates. In total, there were 1,705,306 open reading frames (ORFs) in the 308 genomes, with an average of 5,536 ORFs in each genome. There were 1,800 and 2,392 functional units found in all bovine isolates and human isolates, respectively. Among them, 2,684 functional units were found at a prevalence of >95% in both bovine and human isolates. Nonetheless, there were 177 functional units with significant differences between the human and bovine isolates (P<0.0001). Proteins related to metal ion (iron, zinc, and calcium) metabolism were significantly more prevalent in the bovine isolates; examples included the $Fe^{3+}$ dicitrate transport protein FecA (81.3% versus 43.2%), the zinc protease PqqL (65.9% versus 7%), and the calcium permeable stress-gated cation channel protein TMEM63 (60.2% versus 44.3%).

Example 5

Reverse Vaccinology
Identification of Vaccine Candidates

We used a reverse vaccinology approach to identify protein-expressing genes that could be used as antigens for vaccination. By in silico analysis, we identified 10 genes (yidR, yciD, fepA, entF, ompA, ompX, fhuA, fhuB, creC, and yidE) that were present in all 308 isolates (human and bovine), were highly conserved (>97% DNA homology between all isolates) and which we predicted to have surface-associated antigens. The present disclosure includes these genes, and their protein products, for use in vaccines, alone and in any combination, including in combination with the yidR gene and its encoded protein. The fepA gene encodes outer membrane porin FepA and has been identified as a protective antigen against *K. pneumoniae* (Lundberg et al., 2013). The entF gene share the same enterobactin siderophore loci with fepA in *K. pneumoniae*, that separated by fes gene[31]. EntF is the enterobactin systhase subunit F, acts as a component of the biosynthetic machinery of the enterobactin siderophore[32]. The fhuB gene is a component of fhuDCB operon, encodes protein which specifies the cytoplasmic membrane and periplasmic proteins involved in siderophore uptake and transport[33]. These iron-regulated outer membrane proteins are included within the scope of the present disclosure for use as vaccines because they are surface-exposed, antigenic, and may induce production of antibodies to block iron uptake into the bacterial cells. Furthermore, OmpA is highly represented in the bacterial cell wall, is conserved among the *Enterobacteriaceae*, and is involved in bacterial virulence. OmpX belong to a family of small outer membrane proteins related to virulence. OmpA and OmpX have been characterized as antigen candidates for vaccine development against *K. pneumoniae* infection in humans[34]. FhuA is the ferric hydroxamate outer membrane receptor, the crystal structure of FhuA revealed it could interact with LPS to produce an OMP-LPS complex[35]. The outer membrane proteins have specific LPS binding sites that stabilize a tight interaction with LPS[36], which has the potential to be a candidate target for vaccine development. The CreBC (carbon source-responsive) two-component regulation system involved in catabolic regulation and a variety of functions[37]. CreC may function as an outer membrane protein associated with CreB in response to environmental signals. CreC was observed to affect the growth of bacteria and the accumulation of formate, lactate, acetate, ethanol, and succinate[38]. Finally, YidR and YidE proteins mediated the hyperadherence phenotype and contributed to biofilm formation of *E. coli*[39,40]. The genes yidR, yciD, fepA, entF, ompA, ompX, fhuA, fhuB, creC, and yidE were cloned into the pET vector and expressed in *E. coli* BL-21. A sequence encoding a 6×HIS tag was added to the N-terminus of all genes and protein purification was performed using standard his-tag affinity chromatography methods.

Example 6

Determination of Lethal Dose ($LD_{100}$) of *Klebsiella pneumoniae* in a Murine Peritonitis Model.

To evaluate vaccine candidates, we developed a fatal murine model of peritonitis. From our collection of *Klebsiella pneumoniae* wild strains, we selected a highly virulent strain (C6) for lethal dose determination. This strain was isolated from a milk sample of a CM cow. *K pneumoniae* C6 belongs to sequence type 79 and serotype K62, and harbors 37 virulence genes.

Figure 2:
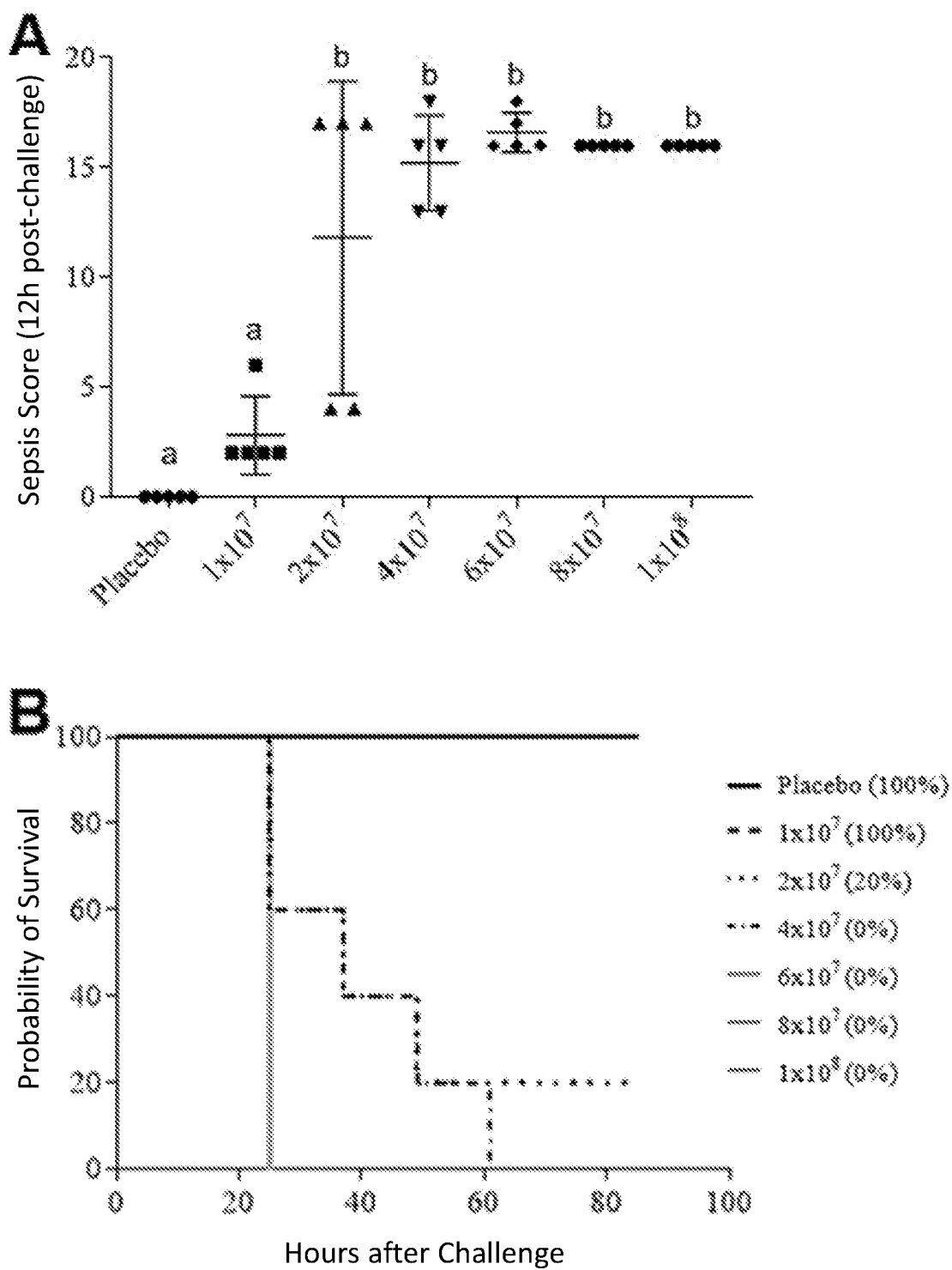
FIG. 2. Determination of lethal dose ($LD_{100}$) using different loads of *Klebsiella pneumoniae* C6. (A) Murine sepsis score (MSS) as a function of *K. pneumoniae* C6; (B) Kaplan-Meier survival curves of mice challenged with different loads of *K. pneumoniae* C6. Different letters indicate significant differences among the bacterial loads tested ($P \leq 0.05$).

An initial dose-finding trial using different bacterial loads of *K. pneumoniae* C6 ($10^3$, $10^4$, $10^5$, $10^6$, $10^7$, and $10^8$ CFU) injected intraperitoneally into mice was carried out to estimate the CFU range of $LD_{100}$. Mice injected with $10^3$-$10^7$ CFU of *K. pneumoniae* C6 recovered from the challenge within 24 h post-inoculation and had few or no signs of disease. Mice injected with $10^8$ CFU of *K. pneumoniae* C6 exhibited significant signs of disease and all mice had to be euthanized within 12 h post-challenge. Therefore, we identified a minimal lethal dose between $10^7$ and $10^8$ CFU for the vaccine trial. Thus, a second study for $LD_{100}$ determination was performed by testing bacterial loads of $1\times10^7$, $2\times10^7$, $4\times10^7$, $6\times10^7$, $8\times10^7$, and $1\times10^8$ CFU of *K. pneumoniae* C6. As expected from the results of the earlier challenge, all mice injected with $1\times10^7$ CFU survived and all mice injected with $1\times10^8$ CFU succumbed to infection (FIG. 3B) and were euthanized according to our IACUC protocol guidelines. The absolute lethal dose of *K. pneumoniae* in this model was identified as $4\times10^7$ CFU, able to kill 100% of mice within 62 h post-challenge (FIG. 2).

Example 7

Evaluation of the protective effect of vaccination in a murine peritonitis model.

An initial trial was performed to screen all 10 proteins (YidR, YciD, FepA, EntF, OmpA, OmpX, FhuA, FhuB, CreC, and YidE) and the YidR protein was the most effective antigen and chosen for further evaluation. In particular, the mortality rate of *K. pneumoniae* challenged mice that were previously vaccinated with recombinant YidR was at least 50% lower when compared to all other experimental vaccines (YciD, FepA, EntF, OmpA, OmpX, FhuA, FhuB, CreC, and YidE).

Fourteen seven-week-old female mice (strain C57BL/6J, Stock#000664, Area AX29, Jackson Laboratory) were injected intraperitoneally with 100 µL of vaccine containing 1,000 ng of YidR protein, and 20% of vaccine adjuvant (2%, aluminum hydroxide gel, Alhydrogel® adjuvant, InvivoGen, CA, USA). Two vaccinations were performed, 7 days apart. Sixteen seven-week-old female mice (strain C57BL/6J, Stock#000664, Area AX29, Jackson Laboratory) were enrolled in the control group, which received 1×PBS, pH 7.4, only. Blood samples were collected from the tail veins of both immunized and mock-immunized mice 7 days from the last immunization to evaluate antibody production. The blood samples were centrifuged, and the serum samples were stored at −20° C. Three weeks after the last immunization, all mice (immunized and non-immunized) were challenged with *K. pneumoniae*-C6. Before lethal challenge, all cages were coded and reorganized to blind the researchers. The mice were injected intraperitoneally with $4\times10^7$ CFU of *K. pneumoniae*-C6 in 1×PBS. Mice were evaluated hourly during the first 12 h post-inoculation, then every 2 h until 24 h post-inoculation, and then evaluated twice per day during the next 10 days. Evaluations were carried out for each mouse by using Murine Sepsis Score (MSS) for each time point, and the body weight was checked daily. Surviving mice were euthanized at the end of the experiment.

Figure 3:
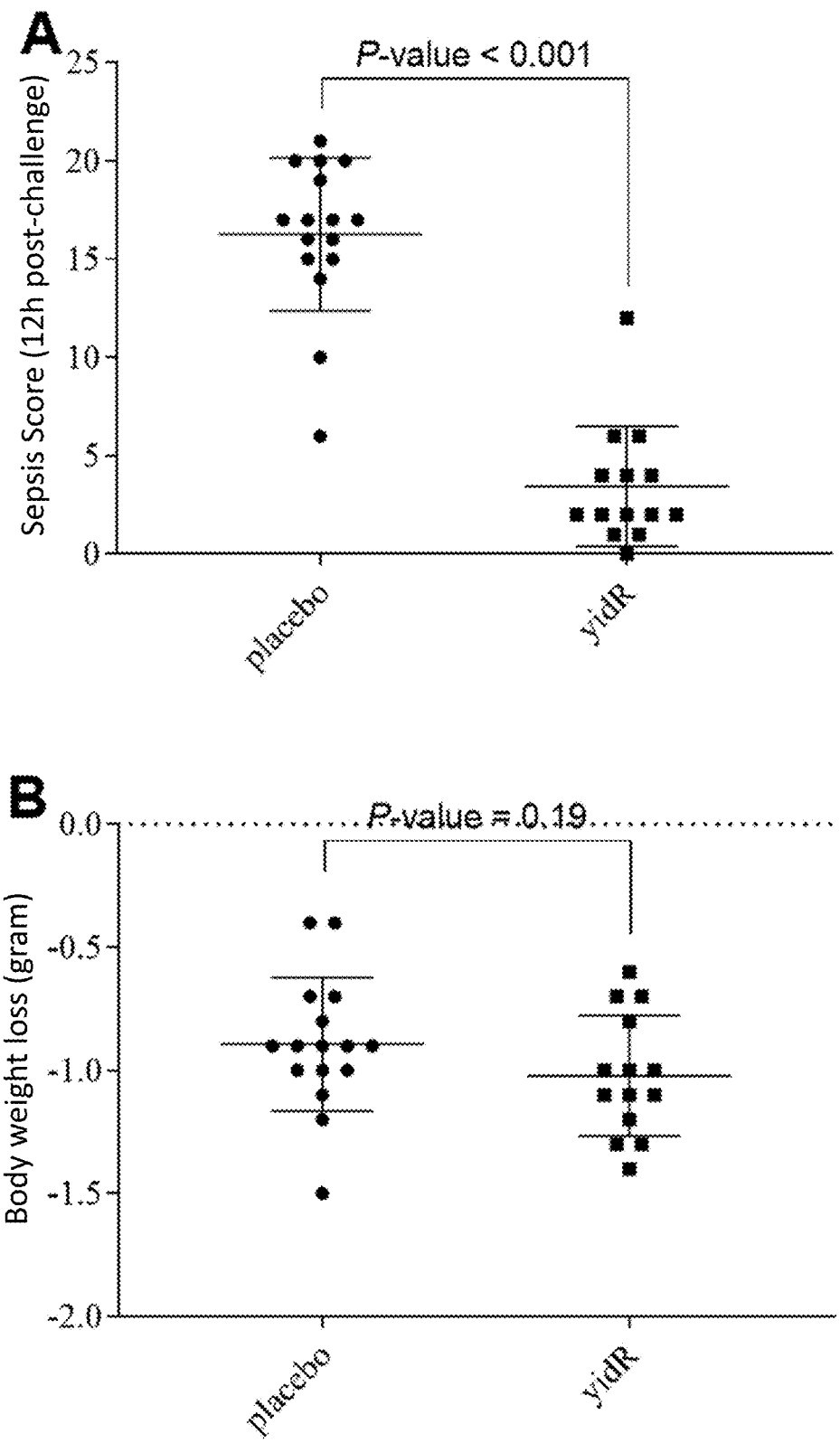
FIG. 3. Immunological assessment. (A) Murine sepsis score of immunized and non-immunized mice 12 hours post-challenge with *Klebsiella pneumoniae* C6; (B) Body weight loss of immunized and non-immunized mice post-challenge; (C) Kaplan-Meier survival curves of immunized and non-immunized mice post-challenge; (D) Optical density values at 650 nm from enzyme-linked immunosorbent assay to detect total immunoglobulin G (IgG) in serum of non-immunized and immunized mice.
Figure 3:
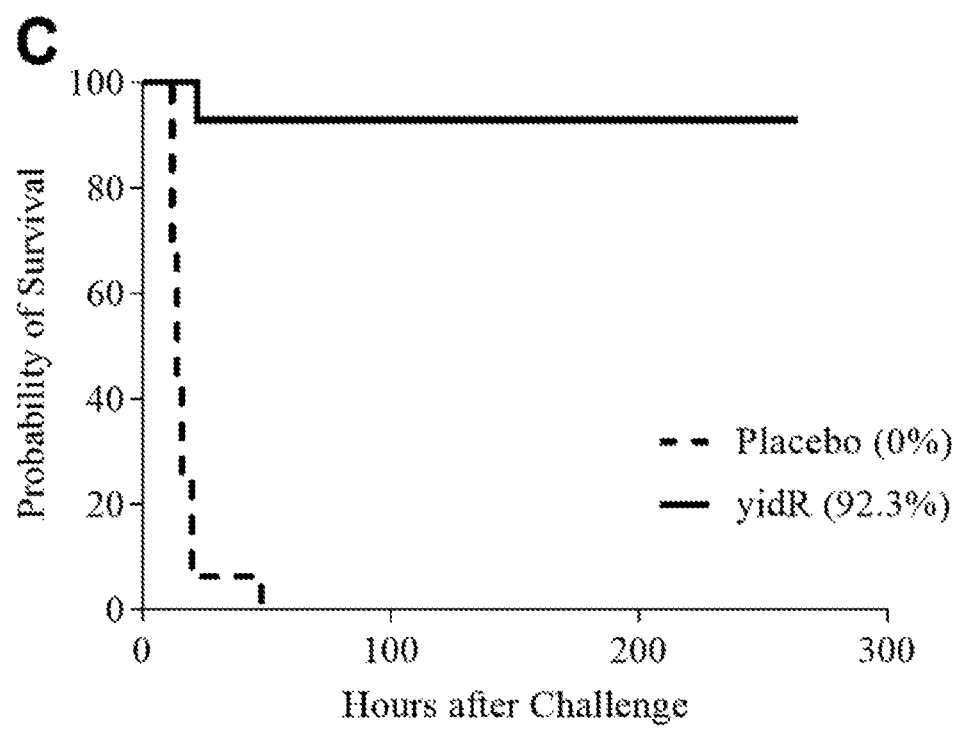
Figure 3:
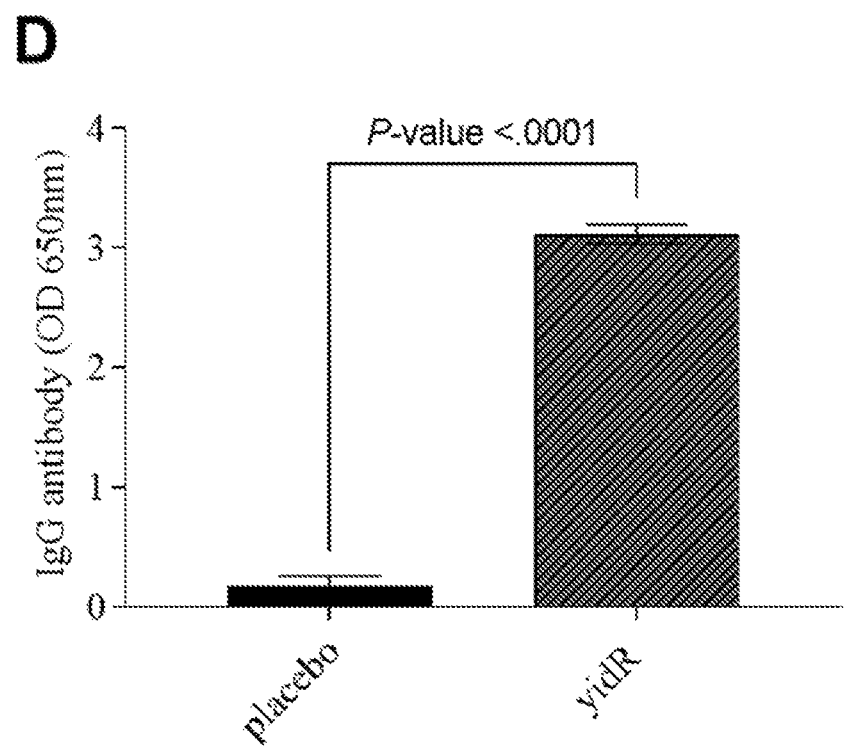

Evaluation post-challenge showed a significant difference in disease manifestation between the rYidR-immunized and non-immunized (control) groups. Twelve hours post-challenge, the MSS was significantly lower (P-value<0.001) in the rYidR mice (FIG. 3A), and body-weight loss was numerically higher (P-value=0.19) in the control group (FIG. 3B). None of the non-immunized mice survived beyond 48 h (FIG. 3C). In contrast, the rYidR group showed a survival rate of 92.3% (FIG. 3C), indicating the strong protective effect of the vaccine. An ELISA assay was conducted to compare the concentration of immunoglobulin G (IgG) in the immunized and control groups. The concentration of total serum IgG was significantly higher in the immunized mice (P-value<0.0001) (FIG. 3D).

Example 8

Mid-Scale Production and Purification of rYidR
Composition of Chemically Defined Medium and Fermentation Parameters.

Fermentation was optimized and performed using a Bioflo® & Celligen® 310 Fermenter/Bioreactor unit (New Brunswick Scientific, NJ, USA) using a fed-batch fermentation method. Bioengineered *E. coli* BL21, containing the yidR plasmid, was cultured in chemically defined medium according with[41]. The composition of the initial fermentation medium was; 450 mL 10× phosphate/citric acid buffer (133 g/L $KH_2PO_4$, 40 g/L $(NH_4)_2HPO_4$, 17 g/L citric acid), 4.05 L deionized (DI) water. The vessel containing the initial medium was autoclaved for 90 min. After the vessel was removed from the autoclave the medium was cooled to room temperature and the following ingredients were added; 45 mL of 240 g/L $MgSO_4$, 1.02 mL of 20 g/L thiamine, 45 mL of 100× trace element solution, and 66 mL of 70% glucose solution. The concentrated trace element solution was prepared, and filter sterilized as follows; 10 g/L iron (III) citrate, 0.25 g/L $CoCl_2 \cdot 6H_2O$, 1.5 g/L $MnCl_2 \cdot 4H_2O$, 0.15 g/L $CuCl_2 \cdot 6H_2O$, 0.3 g/L $H_3BO_3$, 0.25 g/L $Na_2MoO_4 \cdot 2H_2O$, 1.3 g/L zinc acetate·$2H_2O$, 0.84 g/L EDTA. Finally, ampicillin was added to the initial medium to a final concentration of 30 µg/ml. A concentrated feeding medium was prepared in a 2 L glass bottle; 197.1 mL of 240 g/L $MgSO_4$, 7.47 mL of 20 g/L thiamine solution, 67.5 mL of 100× trace element solution, and 70% glucose solution was added to a final volume of 2 L.

The bioreactor was equipped with calibrated probes for pH, temperature, foam level, and dissolved oxygen (DO). A solution of 30% ammonium hydroxide was automatically pumped (Pump 1) into the vessel to maintain the pH at 6.8. A 20% antifoam solution (Antifoam B Emulsion, aqueous-silicone emulsion, Sigma Life Science) was automatically pumped (Pump 2) into the vessel as needed. Pump 3 was assigned to the feeding medium. The feeding strategy was designed to maximize the bacterial growth without the accumulation of glucose in the medium while maintaining DO levels at 25%. To maintain DO levels around 25%, a calibrated DO probe was used and medical grade Oxygen sparging and agitation speed (100-1200 rpm) was automatically adjusted as needed.

The batch fermentation was carried out for 12 hours at 30° C. Then, the fed-batch fermentation begun by adding increasing levels of the concentrated feeding medium using pump 3 which was adjusted manually. Glucose concentration was monitored hourly using DO spikes, which allowed us to control the optimal glucose concentration. Samples were collected every hour to verify the cell growth by measuring wet cell weight (WCW) and OD (600 nm). For WCW determination, 30 mL of culture were collected and centrifuged (4,200 rpm/40 min, 4° C.), and the supernatant was removed[41]. When WCW was reached 50%, protein expression was induced with IPTG (1 mM final concentration), temperature lowered to 25° C., and the concentrated feeding medium reduced to 27 mL/h; the induction of protein expression was completed in 24 hours. Cells were harvested using a continuous flow centrifuge (Carr Powerfuge Pilot, Barry-Wehmiller, MO, USA) at 15,000 rpm. Pellets of cells were resuspended in 1× buffer A (50 mM $NaH_2PO_4$; 300 mM NaCl, pH 7.4) and sonicated on ice, performing 5-min pulses for 5 times, with 5-min intervals. A Misonix Ultrasonic Liquid Processor Q500 (QSonica LLC, CT, USA) was used at 80% amplitude. Sonicated cells were centrifuged (12,000 rcf/30 min, 4° C.) and the supernatant was stored at 4° C. for purification.

Example 9 rYidR Protein Purification.

The clear lysate obtained was processed using a custom-packed 150 mL column of TALON® Metal Affinity Resin (Tanaka Bio USA Inc., CA, USA). The automated purifications were performed based on immobilized metal-affinity chromatography followed by desalting using an AKTA Pure (GE Healthcare, IL, USA) chromatography system controlled by UNICORN 7 software (GE Healthcare, IL, USA). The column, equilibrated with 1× buffer A (50 mM $NaH_2PO_4$; 300 mM NaCl, pH 7.4), was loaded with lysate and the elution was performed using 1× buffer B (150 mM imidazole; 50 mM $NaH_2PO_4$; 300 mM NaCl, pH 7.4). The concentration of 1× buffer B was increased from 0% to 100% in a linear gradient, over 10 column volumes and purified eluded protein was collected using an automated fraction collector. The purified protein was desalted using a 1,200-mL Sephadex G-25 (GE Healthcare, IL, USA) column. The final protein product was sterilized by filtration using a 0.22 µm vacuum filter system (Millipore Sigma, MA, USA). The purified and sterilized protein was quantified using a Quick Start™ Bradford Protein Assay (Bio-Rad, CA, USA) and stored in 50% glycerol at −20° C.

rYidR Protein Production Yield.

Figure 4:
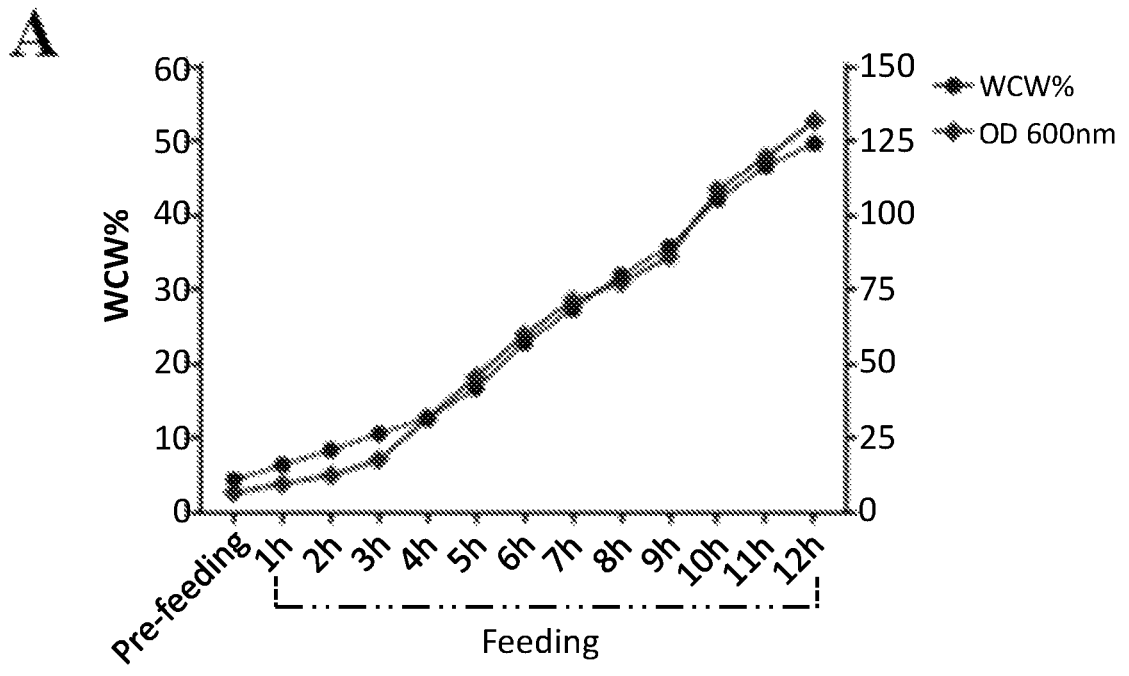
FIG. 4. Overview of rYidR protein production and purification. (A) Growth curve of an *E. coli* BL21(DE3) clone harboring pET-6×His/6his-yidR vector. This illustration shows wet cell weight (WCW %) and optical density (OD) starting at the end of the batch fermentation (12 hours post-inoculation) and throughout the fed-batch period (12 hours); (B) Stained SDS-PAGE gel of whole-cell lysates showing expressed YidR protein following IPTG induction (left panel) and Western blot probed with 6×His antibodies showing his-tagged rYidR protein post-induction (right panel); (C) Stained SDS-PAGE gel showing protein fractions obtained from chromatographic separation.
Figure 4:
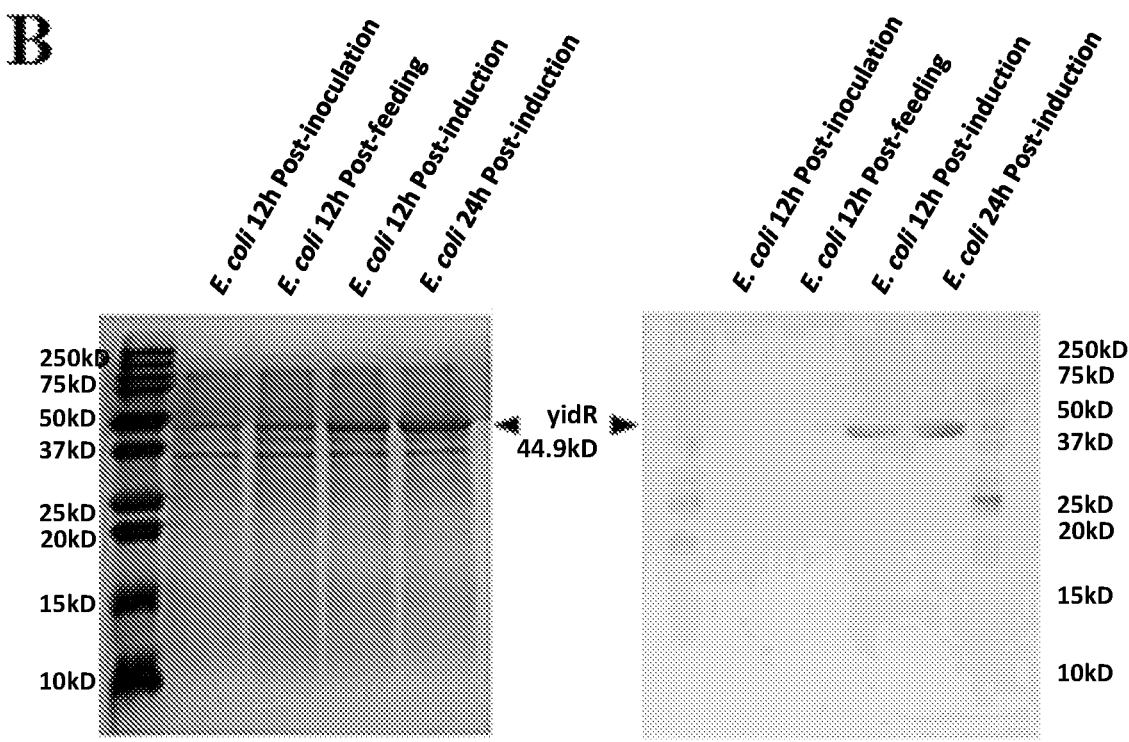
Figure 4:
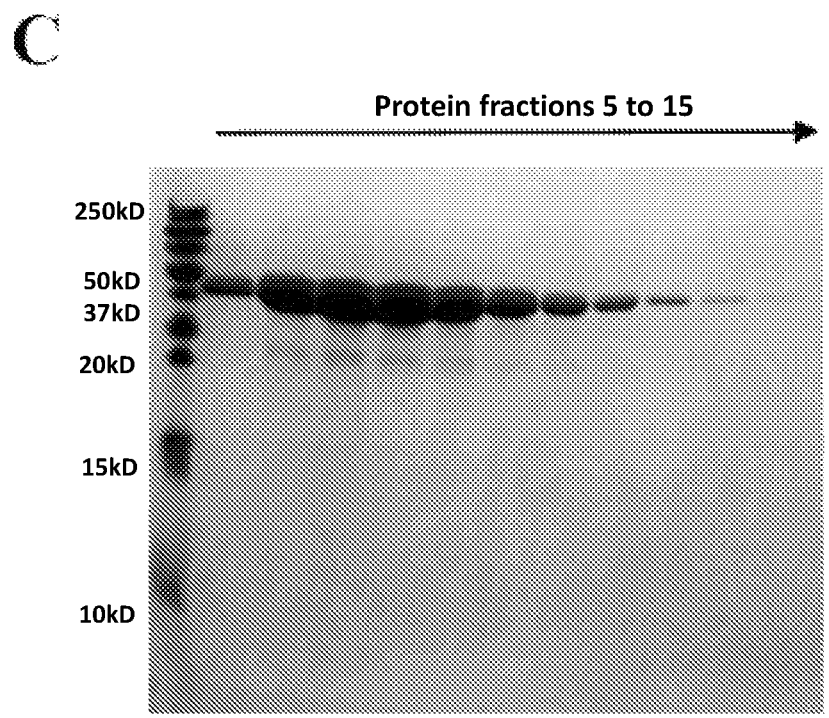

Fermentation using a bioreactor produced a high density of *E. coli* at 24 h (12 h pre-feeding and 12 h fed-batch). The WCW achieved in 24 h was 50% (FIG. 4A). Then, the protein-induction phase was initiated and conducted for 24 h. Culture samples were collected directly from the fermenter vessel to verify protein expression. These samples were submitted to SDS-PAGE and Western blot analysis. The expected recombinant protein band size was identified in a stained SDS-PAGE gel (FIG. 4B, left panel) 12 h and 24 post-induction. A Western blot probed with anti-histidine antibodies confirmed the presence of 6×-His tagged rYidR protein, as shown in FIG. 4B (right panel). After bacterial cell processing, the target protein in the supernatant was purified by chromatography using an elution buffer gradient (0% to 100%). The peak fractions identified were subjected to SDS-PAGE (FIG. 4C) to confirm separation of the rYidR protein. The selected fractions (fractions 5 to 15) were pooled, desalted and sterilized, and glycerol was added for storage at −80° C.; the final protein concentration was 1.8 mg/mL. A final yield of 1.28 grams of purified rYidR was achieved for every litter of *E. coli*-BL21 culture. Therefore, one fermentation run of the 8-liter bioreactor yielded 10,240 mg of rYidR protein. Which is enough to vaccinated 20,480 animals (0.5 mg/dose).

Example 10

Large Double Blinded, Placebo Controlled, Randomized Clinical Trial to Evaluate the Effect of rYidR Vaccine or a Commercially Available Vaccine (KLEBvax™) on the Incidence of Clinical Mastitis by *Klebsiella* spp. and *E. coli*.

This trial was carried out in strict accordance with the recommendations of The Animal Welfare Act of 1985 (P.L. 99-198). The research protocol was reviewed and approved by the Institutional Animal Care and Use Committee of Cornell University.

The objective of the study was to evaluate the efficacy of a commercially available bacterin vaccine (KlebVax™; USDA registered and commercially available in the USA), a novel recombinant subunit vaccine containing the protein rYidR as described herein, against placebo treated cows. A total of 3,107 cows were blocked by parity group (nulliparous, primiparous, and multiparous) and randomly allocated into one of 3 treatment groups: placebo (1,045 cows), KlebVax™ (1,026 cows), and rYidR (1,036 cows). Cows received two vaccinations: 220±3 days of pregnancy and 241±3 days of pregnancy (Table 1), e.g., given the bovine gestation length of 280 days on average, the cows were vaccinated 220 and 241 days into the gestation. All cows received 1 milligram of the rYidR protein in a 2-milliliter solution, administered subcutaneously. 20% of the final vaccine was the adjuvant and the adjuvant solution had a concentration of 2% of aluminum hydroxide. Thu, in the 2 milliliter solution, 0.4 milliliters was a 2% aluminum hydroxide solution. Control cows received a placebo and all research personnel were blinded to vaccination treatment. Vaccines and placebo preparations were stored in identical containers and labeled "A", "B", and "C". Treatments were undisclosed to the persons administering the treatment, examining the cows, collecting clinical data, or to farm personnel. The code was only broken at the end of the follow-up period and after all data were analyzed.

The study described in this Example was conducted on a large commercial dairy farm located in Cayuga County near Ithaca, New York, USA. The farm was milking 4,000 Holstein cows thrice daily in a 100-stall rotary milking parlor with integrated milk meters that recorded individual production at every milking (DeLaval, Tumba, Sweden).

Clinical mastitis was diagnosed during each milking by trained farm personnel, who were instructed to detect abnormal changes in the udder and milk, such as watery appearance, flakes and clots in milk and visual evidence of udder inflammation. All CM cases were sampled and mastitic milk samples were submitted to the Cornell QMPS laboratory; results were automatically downloaded into the farm's DC-305 software daily. All intramammary treatment was dependent upon culture results; the farm only administered intramammary antibiotic treatment to cows with *Streptococcus* spp. and non-aureus Staphylococcus mastitis. All culture results from clinical mastitis cases were stored in the farm's DC305 software.

All cows enrolled in the study were followed for a minimum of 200 days postpartum. The primary variable of interest was the incidence of CM associated with *Klebsiella* spp. during the follow-up period. Other variables of interest were: incidence of clinical mastitis associated with other pathogens, milk production, linear score of SCC, incidence of metritis, and conception at first service.

TABLE 1

Descriptive statistics data describing the random groups

| Item | Treatment | | | P-value |
| --- | --- | --- | --- | --- |
| | Control | rYidR | KlebVAX | |
| Enrolled cows | 1,045 | 1,036 | 1,026 | 0.86 |
| Nulliparous | 380 | 373 | 367 | 0.99 |
| First lactation | 284 | 279 | 268 | |
| Second lactation | 173 | 172 | 175 | |
| Third or more lactation | 208 | 212 | 216 | |
| Days carried calf (1$^{st}$ vaccination) | 220 | 221 | 221 | 0.63 |
| Age in days | 1,132 | 1,136 | 1,135 | 0.99 |

Example 11

Figure 5:
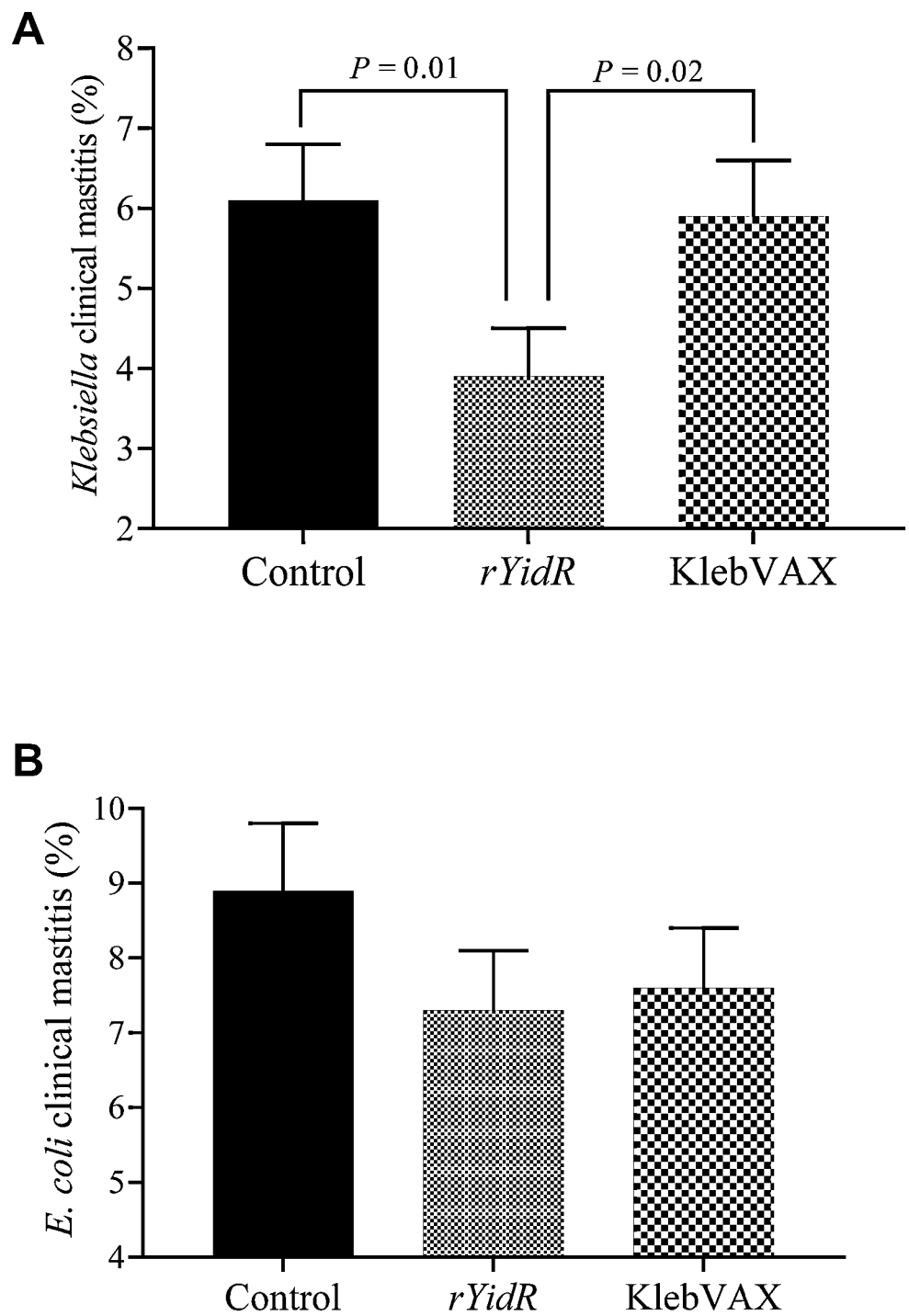
FIG. 5: Graphic panel describing the effect of vaccination group (placebo control, rYidR, KlebVAX™) on the incidence of clinical mastitis by *Klebsiella* spp. (A) and *E. coli* (B), milk production (C), and linear score (D). Serum and IgG (E) and IgM (F) response to vaccination are also depicted.
Figure 5:
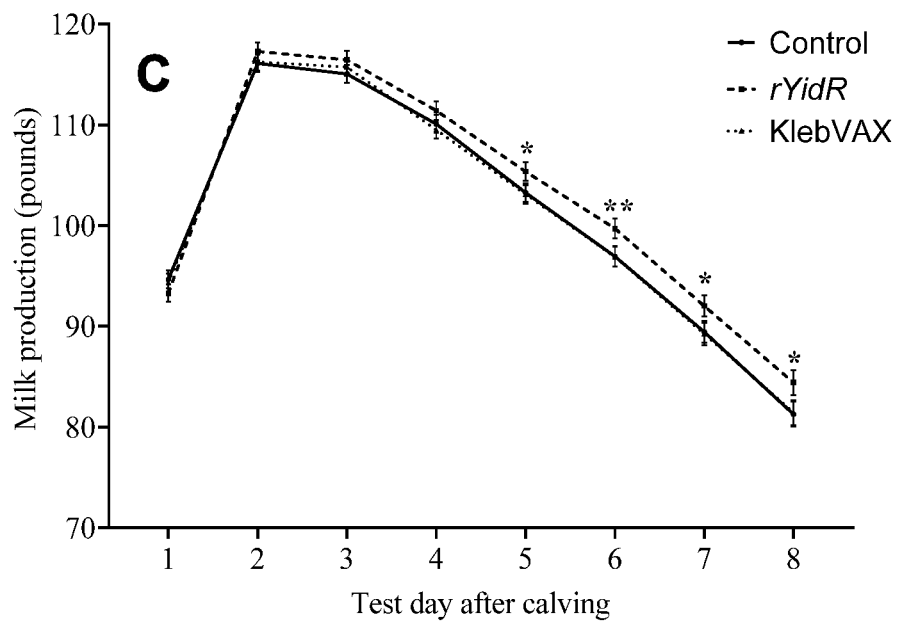
Figure 5:
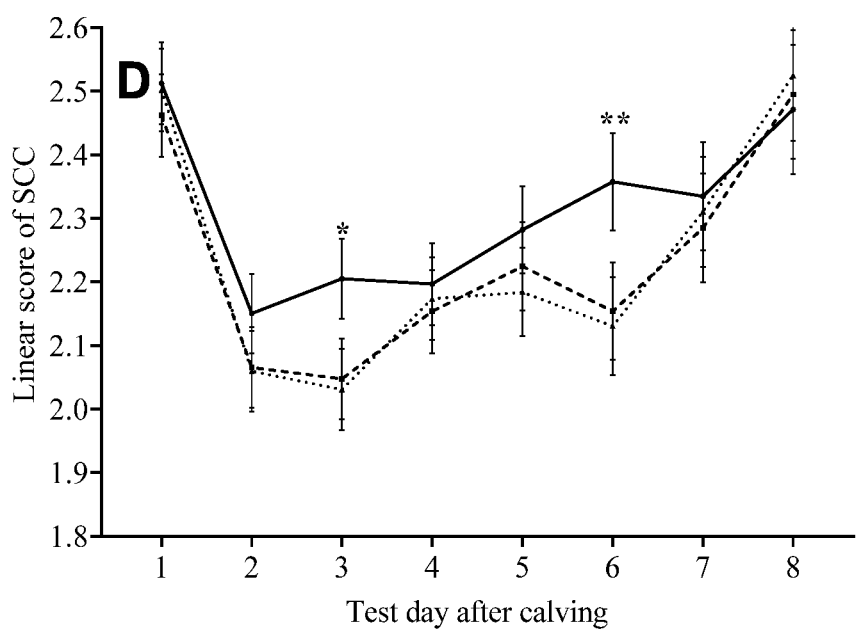
Figure 5:
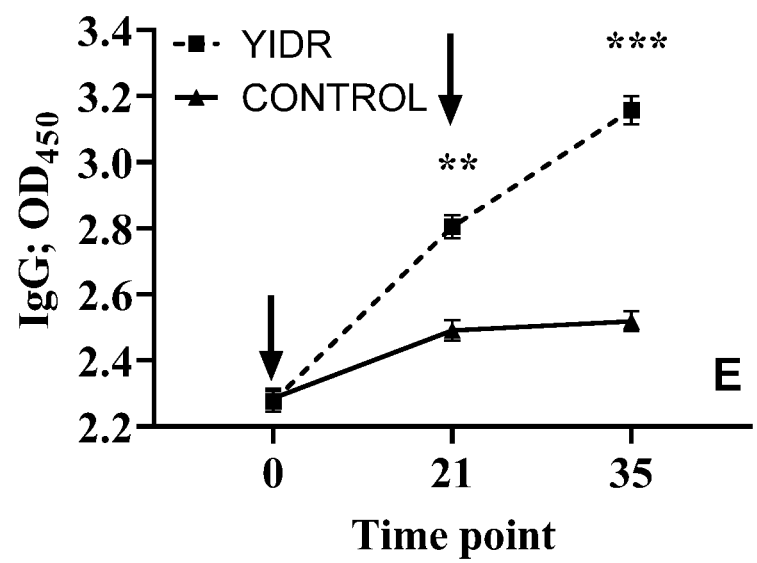
Figure 5:
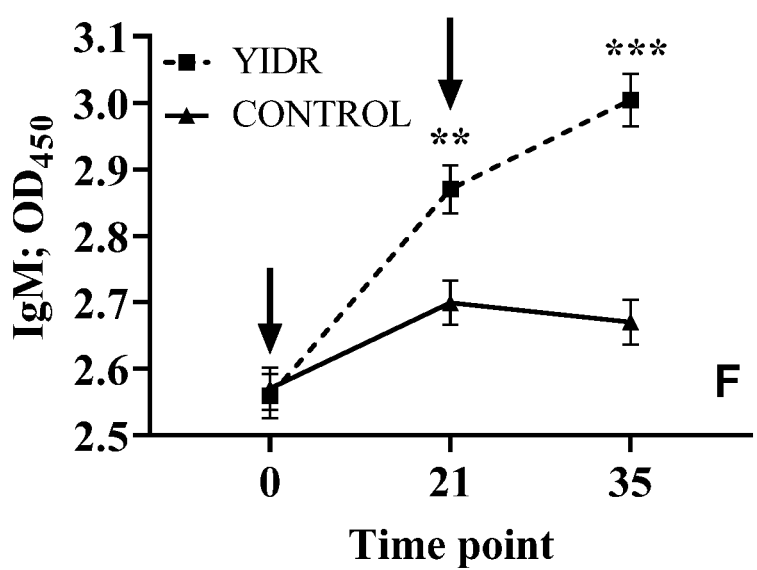

Vaccination with rYidR Significantly Reduced the Incidence of Clinical Mastitis by *Klebsiella* spp. When Compared to Placebo (P=0.01) and KlebVAX (P=0.02) Vaccinated Groups (FIG. 5-A).

Figure 6:
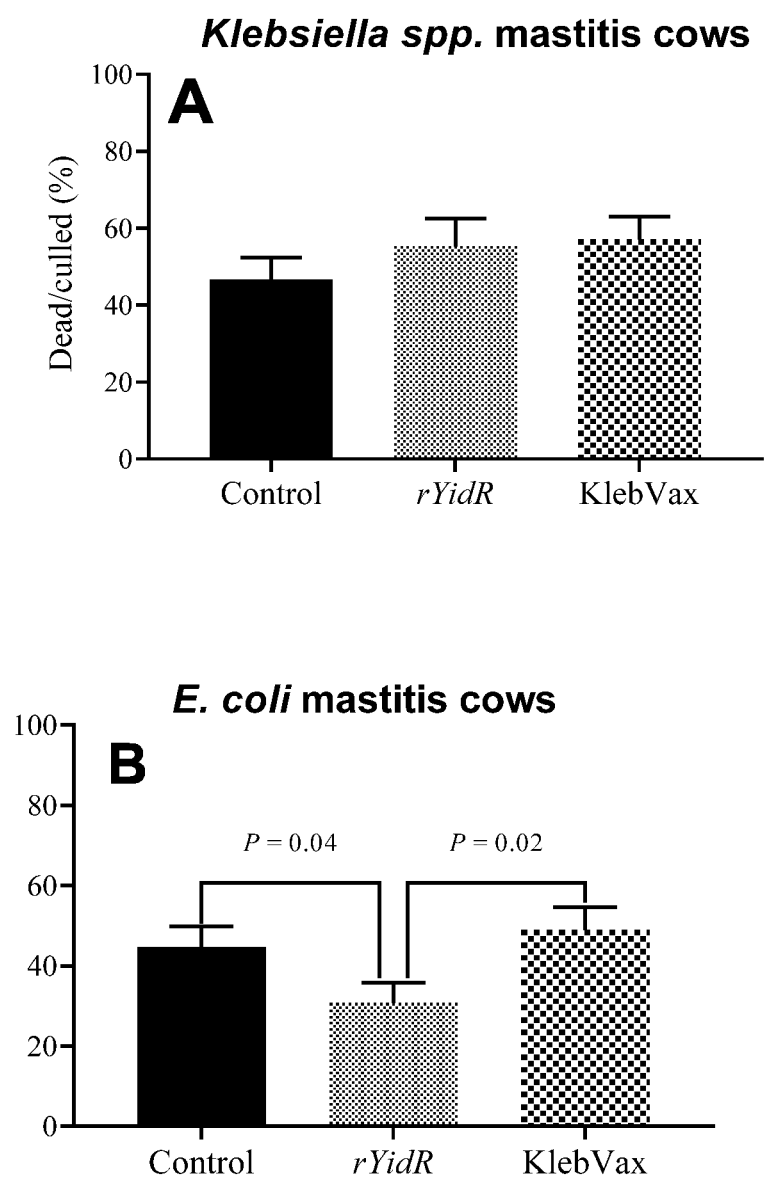
FIG. 6: Effect of vaccination on survival (A and B) and milk production (C and D) following the diagnosis of *Klebsiella* spp. (A and C) or *E. coli* (B and D) mastitis.
Figure 6:
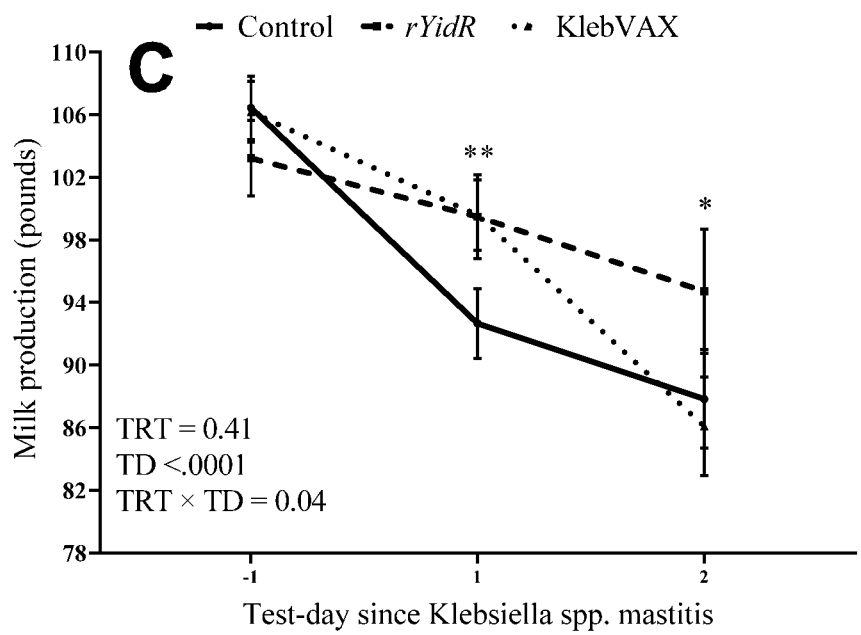
Figure 6:
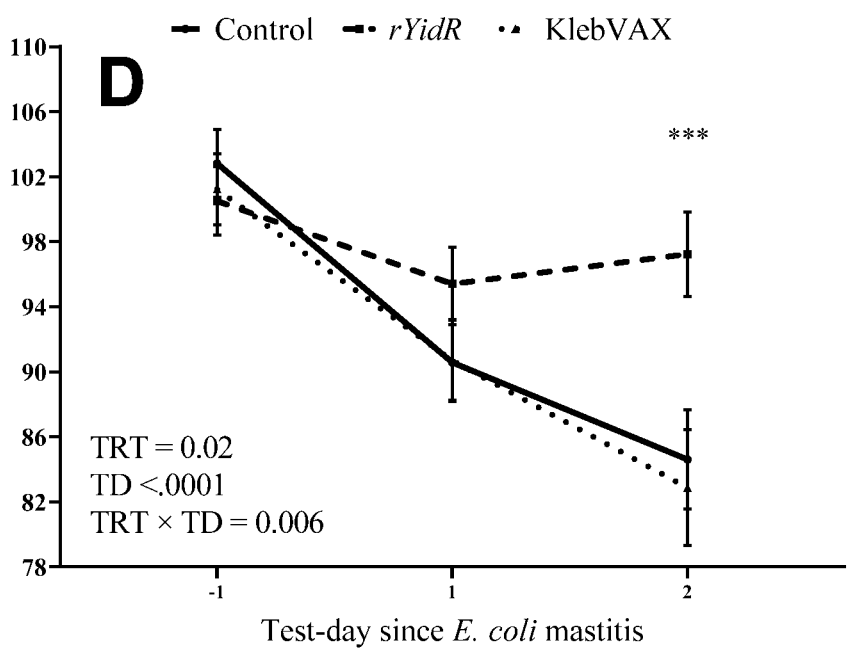

The use of KlebVAX™, a USDA-registered vaccine against *Klebsiella* spp. mastitis, as described above, did not reduce the incidence of *Klebsiella* spp. mastitis; 5.9% of KlebVAX vaccinated cows developed *Klebsiella* spp., whereas 6.1% of the placebo treated cows were diagnosed with *Klebsiella* spp. CM (FIG. 5-A). A numerical reduction of *E. coli* CM was observed for rYidR and KlebVAX™ vaccine groups when compared to placebo treated animals (FIG. 5-B). Animals vaccinated with rYidR vaccine produced significantly more milk than placebo and KlebVAX™ treatment groups (FIG. 5-C) and both rYidR and KlebVAX™ treatment groups had significantly lower linear scores when compared to placebo treated animals (FIG. 5-D). Although rYidR vaccination significantly decreased the incidence of *Klebsiella* spp. mastitis (FIG. 5-A), the animals that were affected with *K. pneumoniae* mastitis were at a similar risk of mortality/culling following the mastitis event, regardless of treatment group (P=0.68). Antigen-specific IgG and IgM was measured in serum samples using ELISA and the purified rYidR protein as the capture antigen. Vaccination with rYidR protein elicited a strong seroconversion measured both by IgG and IgM levels in serum. However, milk production at 30 and 60 days after the diagnosis of *Klebsiella* spp. mastitis was significantly higher for animals in the rYidR vaccination group (FIG. 6-C). KlebVAX™ vaccinated cows that were affected with *Klebsiella* spp. mastitis also produced more milk at 30 days after the mastitis event when compared to control cows, but not at 60 days following the diagnosis of the mastitis case. Hence, vaccination was associated with decreased clinical severity of *Klebsiella* spp. mastitis. Unexpectedly, rYidR vaccinated cows that were diagnosed with *E. coli* mastitis, experienced a dramatic reduction in the probability of mortality/culling and produced more milk following mastitis diagnosis when compared to control and KlebVAX™ groups (FIG. 6-BD). The increase in milk production likely occurred in all vaccinated cows (e.g., including non-mastitic cows) because milk production data represent all cows, and only a small portion of the cows were diagnosed with *Klebsiella mastitis*.

Example 12

Figure 7:
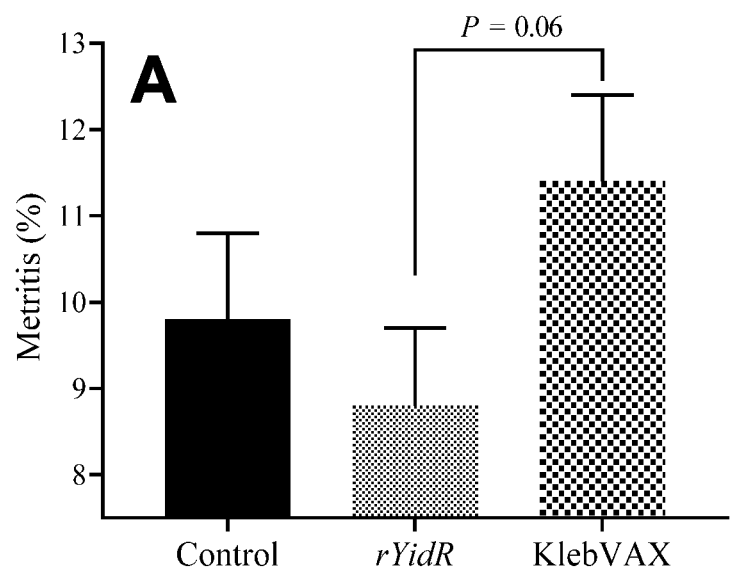
FIG. 7: Effect of vaccination on the incidence of metritis (A), overall first service conception rate (B), primiparous first service conception rate (C), and multiparous first service conception rate (D).
Figure 7:
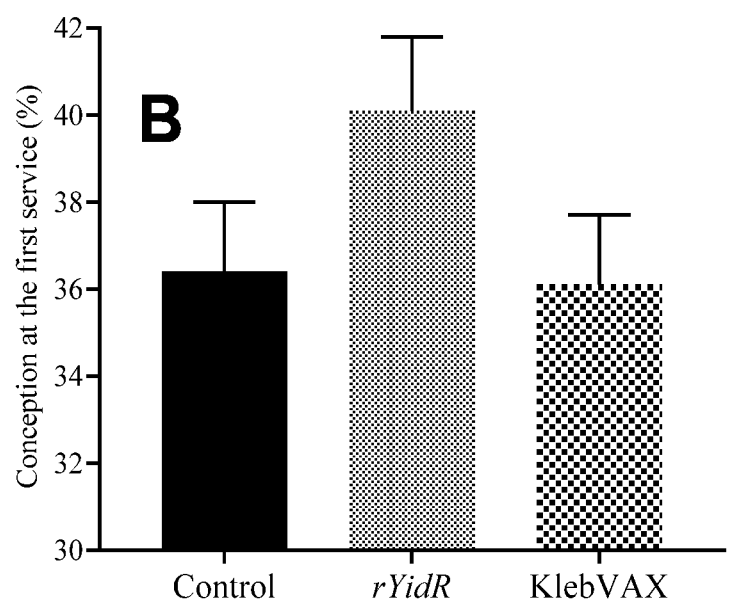
Figure 7:
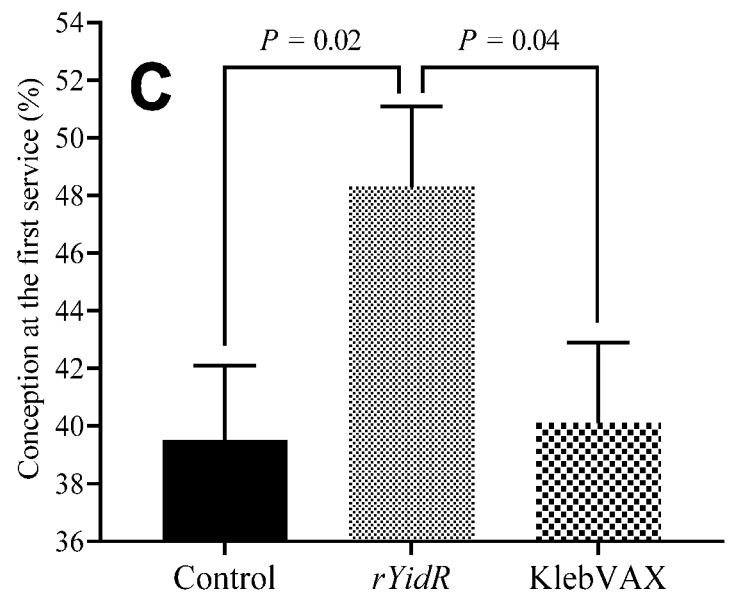
Figure 7:
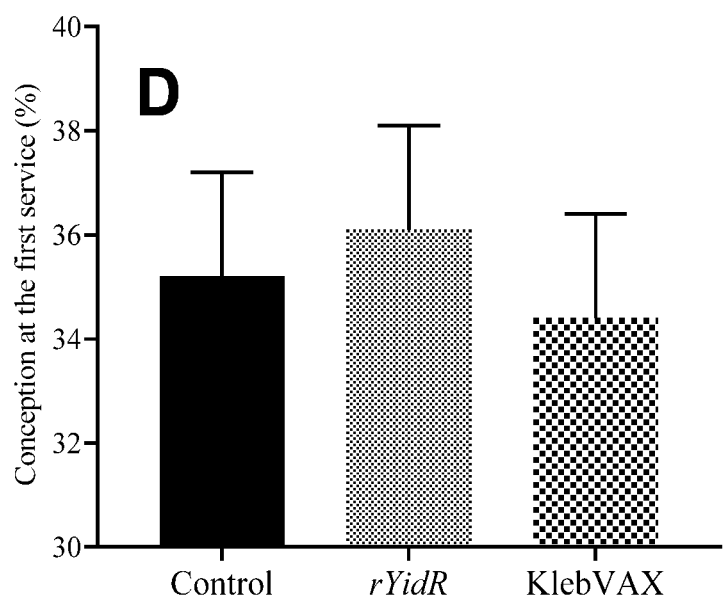

Effect of Vaccination on the Incidence of Metritis and Conception Rate at First Service It was not an initial objective of the described study to evaluate the effect of vaccination on the incidence of metritis. However, given the strong effects of rYidR vaccination on the incidence and severity of *E. coli* mastitis and given that *E. coli* is associated with metritis we decided to analyze the effect of vaccination on metritis and first service conception rate (FIG. 7 A-D). KlebVAX™ vaccinated animals tended to have a higher risk of developing metritis when compared to rYidR and placebo vaccinated animals. The incidence of metritis was numerically lower in the rYidR group. Importantly, first service conception rate was higher for the rYidR group. This increased conception rate was mainly driven by the effect in primiparous animals (FIG. 7 C). Primiparous animals are known to be at higher risk of metritis compared to multiparous which could help explain this effect. Additionally, the detrimental effect of Gram-negative mastitis on reproductive performance is well understood by the scientific community and the preventative effect of rYidR vaccination on mastitis incidence may partially explain the improved reproductive performance. As is known in the art, metritis is based on the appearance of the uterine secretion with or without fever.

Figure 8:
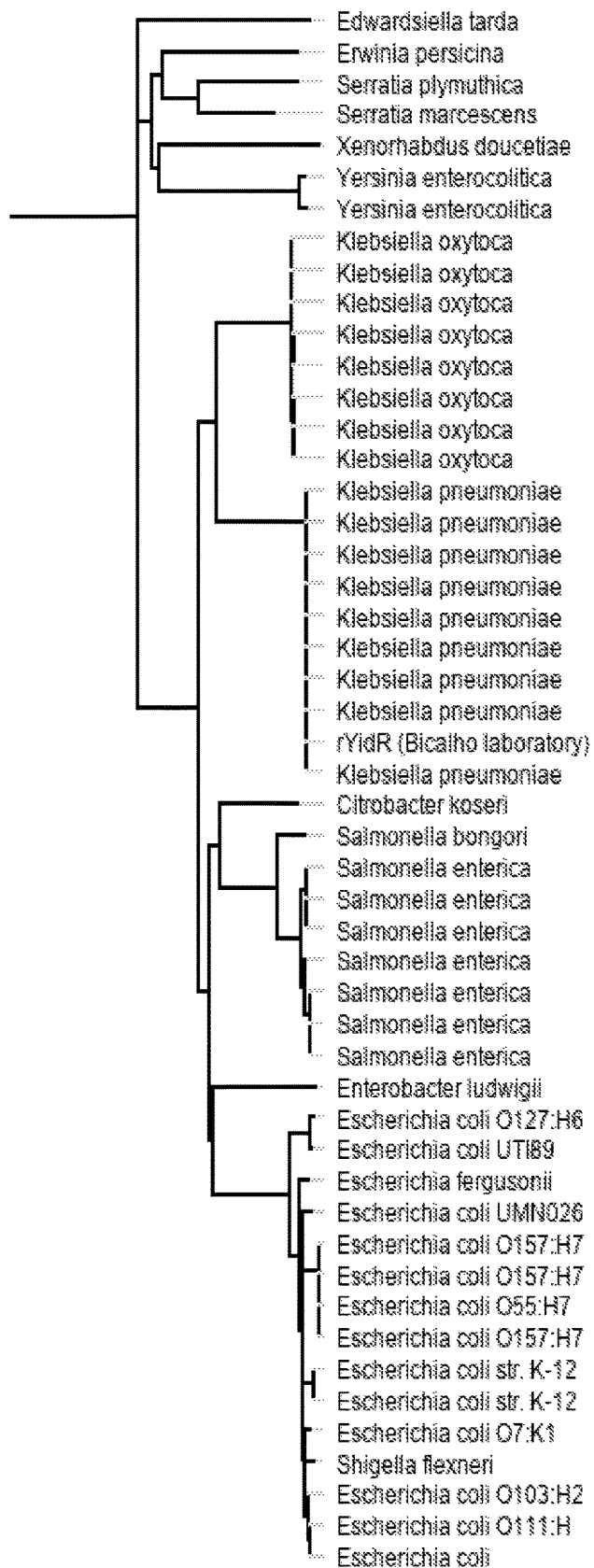
FIG. 8: Phylogenetic tree illustrating the similarity of nucleotide sequences of the yidR gene of several species of Gram-negative bacteria.

The results of the above described randomized, double blinded, placebo-controlled trial clearly indicate that vaccination against the subunit rYidR, originated from a sequence extracted from a *Klebsiella pneumonia* isolate, cross-protected animals against *E. coli* mastitis (FIG. 5-B, 6-BD). Very little is known about the YidR protein and its potential biological functions. Without intending to be bound by any particular theory, prior to the present disclosure which provides a demonstration of cloning and expressing the yidR gene, the YidR protein was simply classified as uncharacterized putative protein YidR (www.uniprot.org/uniprot/P31455). Kroupitski et. al. (2013), is the only published work that has attempted to elucidate the function of the yidR gene[42]. In this reference, it was demonstrated that when the yidR gene was deleted from a *S. enterica* strain its ability to adhere to lettuce leaves was considerably reduced as well as its ability to form biofilm. Using the aligned nucleotide sequences of yidR genes from several species of Gram-negative bacteria we built the phylogenetic tree illustrated on FIG. 8. There is a high level of sequence homology observed within each species and between all coliforms and the *Salmonella* genus. The species level nucleotide sequence pairwise identity was 99.6%, 100%, 96%, 98.7% for the *K. oxytoca, K. pneumoniae, E. coli,* and *Salmonella enterica*, respectively. When the amino acid sequence of the rYidR protein was aligned against the sequences of an *E. coli* 0157:H7 and *S. enterica* str. SC-B67 a pairwise identity of 79% and 80% was determined, respectively. Predicted antigenic regions and secondary structures were also very similar between the 3 different species (Table 2). In Table 2, "Minimum" refers to the N-terminal amino acid of each segment, "Maximum" refers to the C-terminal end of each segment, and "Length" refers to the number of amino acids in each segment. Each predicted antigenic segment of each protein as described in Table 2 is encompassed by this disclosure.

TABLE 2

|  | Minimum | Maximum | Length |
| --- | --- | --- | --- |
| rYidR *Klebsiella* | 364 | 384 | 21 |
| rYidR *Klebsiella* | 351 | 360 | 10 |
| rYidR *Klebsiella* | 325 | 334 | 10 |
| rYidR *Klebsiella* | 308 | 318 | 11 |
| rYidR *Klebsiella* | 297 | 303 | 7 |
| rYidR *Klebsiella* | 277 | 290 | 14 |
| rYidR *Klebsiella* | 262 | 271 | 10 |
| rYidR *Klebsiella* | 250 | 255 | 6 |
| rYidR *Klebsiella* | 230 | 239 | 10 |
| rYidR *Klebsiella* | 213 | 221 | 9 |
| rYidR *Klebsiella* | 182 | 191 | 10 |
| rYidR *Klebsiella* | 154 | 174 | 21 |
| rYidR *Klebsiella* | 144 | 152 | 9 |
| rYidR *Klebsiella* | 136 | 142 | 7 |
| rYidR *Klebsiella* | 125 | 134 | 10 |
| rYidR *Klebsiella* | 115 | 121 | 7 |
| rYidR *Klebsiella* | 96 | 109 | 14 |
| rYidR *Klebsiella* | 74 | 81 | 8 |
| rYidR *Klebsiella* | 61 | 72 | 12 |
| rYidR *Klebsiella* | 44 | 50 | 7 |
| rYidR *Klebsiella* | 23 | 33 | 11 |
| rYidR *Klebsiella* | 4 | 13 | 10 |
| yidR - *Salmonella* | 377 | 384 | 8 |
| yidR - *Salmonella* | 364 | 369 | 6 |
| yidR - *Salmonella* | 345 | 360 | 16 |
| yidR - *Salmonella* | 325 | 336 | 12 |
| yidR - *Salmonella* | 310 | 318 | 9 |
| yidR - *Salmonella* | 297 | 303 | 7 |
| yidR - *Salmonella* | 273 | 282 | 10 |
| yidR - *Salmonella* | 262 | 271 | 10 |
| yidR - *Salmonella* | 216 | 241 | 26 |
| yidR - *Salmonella* | 182 | 191 | 10 |
| yidR - *Salmonella* | 154 | 177 | 24 |
| yidR - *Salmonella* | 144 | 152 | 9 |
| yidR - *Salmonella* | 136 | 142 | 7 |
| yidR - *Salmonella* | 125 | 134 | 10 |
| yidR - *Salmonella* | 115 | 121 | 7 |
| yidR - *Salmonella* | 96 | 104 | 9 |
| yidR - *Salmonella* | 44 | 80 | 37 |
| yidR - *Salmonella* | 23 | 33 | 11 |
| yidR - *Salmonella* | 5 | 13 | 9 |
| YidR - *E. coli* O157:H7 | 388 | 395 | 8 |
| YidR - *E. coli* O157:H7 | 372 | 381 | 10 |
| YidR - *E. coli* O157:H7 | 357 | 370 | 14 |
| YidR - *E. coli* O157:H7 | 321 | 329 | 9 |
| YidR - *E. coli* O157:H7 | 309 | 314 | 6 |
| YidR - *E. coli* O157:H7 | 284 | 305 | 22 |
| YidR - *E. coli* O157:H7 | 271 | 282 | 12 |
| YidR - *E. coli* O157:H7 | 241 | 250 | 10 |
| YidR - *E. coli* O157:H7 | 224 | 233 | 10 |
| YidR - *E. coli* O157:H7 | 193 | 202 | 10 |
| YidR - *E. coli* O157:H7 | 159 | 185 | 27 |
| YidR - *E. coli* O157:H7 | 126 | 145 | 20 |
| YidR - *E. coli* O157:H7 | 107 | 113 | 7 |
| YidR - *E. coli* O157:H7 | 55 | 91 | 37 |
| YidR - *E. coli* O157:H7 | 34 | 44 | 11 |
| YidR - *E. coli* O157:H7 | 4 | 9 | 6 |

It will be recognized from the foregoing that the results of a large double-blinded randomized clinical trial described herein demonstrate that immunization with rYidR protein, but not with the commercial vaccine sold under the trade name KLEBvax™, decreased mortality rates (death and culling) by nearly 40% and lessened milk production losses for animal diagnosed with *E. coli* mastitis. In a presently provided example, all cows were vaccinated with J-5 vaccine twice before parturition (60 and 30 days prepartum) and twice after parturition (35 and 100 days in milk). Hence, the beneficial effects of the rYidR vaccination are improved relative to the effects of the vaccine sold under the trade name KLEBvax™ as well the J-5 vaccine.

The following reference listing is not an indication that any reference(s) is material to patentability.

1 Heikkila, A. M., Liski, E., Pyorala, S. & Taponen, S. Pathogen-specific production losses in bovine mastitis. *J Dairy Sci, doi:*10.3168/jds.2018-14824 (2018).

2 Fogsgaard, K. K., Bennedsgaard, T. W. & Herskin, M. S. Behavioral changes in freestall-housed dairy cows with naturally occurring clinical mastitis. *J Dairy Sci* 98, 1730-1738, doi:10.3168/jds.2014-8347 (2015).

3 Grohn, Y. T. et al. Effect of pathogen-specific clinical mastitis on milk yield in dairy cows. *J Dairy Sci* 87, 3358-3374, doi:10.3168/jds.S0022-0302(04)73472-4 (2004).

4 Schukken, Y. H. et al. Effects of repeated gram-positive and gram-negative clinical mastitis episodes on milk yield loss in Holstein dairy cows. *J Dairy Sci* 92, 3091-3105, doi:10.3168/jds.2008-1557 (2009).

5 Pol, M. & Ruegg, P. L. Treatment practices and quantification of antimicrobial drug usage in conventional and organic dairy farms in Wisconsin. *J Dairy Sci* 90, 249-261, doi:10.3168/jds.S0022-0302(07)72626-7 (2007).

6 Bushnell, R. B. The importance of hygienic procedures in controlling mastitis. *Vet Clin North Am Large Anim Pract* 6, 361-370, doi:10.1016/s0196-9846(17)30029-0 (1984).

7 Olde Riekerink, R. G., Barkema, H. W., Kelton, D. F. & Scholl, D. T. Incidence rate of clinical mastitis on Canadian dairy farms. *J Dairy Sci* 91, 1366-1377, doi:10.3168/jds.2007-0757 (2008).

8 Erskine, R. J., Eberhart, R. J., Hutchinson, L. J., Spencer, S. B. & Campbell, M. A. Incidence and types of clinical mastitis in dairy herds with high and low somatic cell counts. *J Am Vet Med Assoc* 192, 761-765 (1988).

9 Botrel, M. A. et al. Distribution and antimicrobial resistance of clinical and subclinical mastitis pathogens in dairy cows in Rhone-Alpes, France. *Foodborne Pathog Dis* 7, 479-487, doi:10.1089/fpd.2009.0425 (2010).

10 Bannerman, D. D. Pathogen-dependent induction of cytokines and other soluble inflammatory mediators during intramammary infection of dairy cows. *J Anim Sci* 87, 10-25, doi:10.2527/jas.2008-1187 (2009).

11 Rajala-Schultz, P. J. & Grohn, Y. T. Comparison of economically optimized culling recommendations and actual culling decisions of Finnish Ayrshire cows. *Prev Vet Med* 49, 29-39 (2001).

12 Todhunter, D. A., Smith, K. L., Hogan, J. S. & Schoenberger, P. S. Gram-negative bacterial infections of the mammary gland in cows. *Am J Vet Res* 52, 184-188 (1991).

13 Roberson, J. R., Warnick, L. D. & Moore, G. Mild to moderate clinical mastitis: Efficacy of intramammary amoxicillin, frequent milk-out, a combined intramammary amoxicillin, and frequent milk-out treatment versus no treatment. *Journal of Dairy Science* 87, 583-592 (2004).

14 Erskine, R. J., Bartlett, P. C., VanLente, J. L. & Phipps, C. R. Efficacy of systemic ceftiofur as a therapy for severe clinical mastitis in dairy cattle. *Journal of Dairy Science* 85, 2571-2575, doi:DOI 10.3168/jds.50022-0302(02) 74340-3 (2002).

15 Grohn, Y. T. et al. Effect of pathogen-specific clinical mastitis on herd life in two New York State dairy herds. *Prev Vet Med* 71, 105-125, doi:10.1016/j.prevetmed.2005.06.002 (2005).

16 Erskine, R. J., Wagner, S. & DeGraves, F. J. Mastitis therapy and pharmacology. *Vet Clin North Am Food Anim Pract* 19, 109-138, vi (2003).

17 Suoj ala, L., Kaartinen, L. & Pyorala, S. Treatment for bovine *Escherichia coli* mastitis—an evidence-based approach. *J Vet Pharmacol Ther* 36, 521-531, doi: 10.1111/jvp.12057 (2013).

18 Ganda, E. K. et al. Longitudinal metagenomic profiling of bovine milk to assess the impact of intramammary treatment using a third-generation cephalosporin. *Scientific reports* 6, 37565, doi:10.1038/srep37565 (2016).

19 Hogan, J. S. et al. Effects of an *Escherichia coli* J5 vaccine on mild clinical coliform mastitis. *J Dairy Sci* 78, 285-290, doi:10.3168/jds.S0022-0302(95)76636-X (1995).

20 Hogan, J. S., Smith, K. L., Todhunter, D. A. & Schoenberger, P. S. Field trial to determine efficacy of an *Escherichia coli* J5 mastitis vaccine. *J Dairy Sci* 75, 78-84, doi:10.3168/jds.S0022-0302(92)77741-8 (1992).

21 Hogan, J. S., Weiss, W. P., Todhunter, D. A., Smith, K. L. & Schoenberger, P. S. Efficacy of an *Escherichia coli* J5 mastitis vaccine in an experimental challenge trial. *J Dairy Sci* 75, 415-422, doi:10.3168/jds.S0022-0302(92) 77777-7 (1992).

22 Wilson, D. J., Mallard, B. A., Burton, J. L., Schukken, Y. H. & Grohn, Y. T. Association of *Escherichia coli* J5-specific serum antibody responses with clinical mastitis outcome for J5 vaccinate and control dairy cattle. *Clin Vaccine Immunol* 16, 209-217, doi:10.1128/CVI.00324-08 (2009).

23 Gonzalez, R. N. et al. Prevention of clinical coliform mastitis in dairy cows by a mutant *Escherichia coli* vaccine. *Can J Vet Res* 53, 301-305 (1989).

24 Dosogne, H., Vangroenweghe, F. & Burvenich, C. Potential mechanism of action of J5 vaccine in protection against severe bovine coliform mastitis. *Vet Res* 33, 1-12, doi:10.1051/vetres:2001001 (2002).

25 Wilson, D. J. et al. Milk production change following clinical mastitis and reproductive performance compared among J5 vaccinated and control dairy cattle. *J Dairy Sci* 91, 3869-3879, doi:10.3168/jds.2008-1405 (2008).

26 Wilson, D. J. et al. Comparison of J5 vaccinates and controls for incidence, etiologic agent, clinical severity, and survival in the herd following naturally occurring cases of clinical mastitis. *J Dairy Sci* 90, 4282-4288, doi:10.3168/jds.2007-0160 (2007).

27 Schukken, Y. et al. The "other" gram-negative bacteria in mastitis: *Klebsiella, serratia*, and more. *Vet Clin North Am Food Anim Pract* 28, 239-256, doi:10.1016/ j.cvfa.2012.04.001 (2012).

28 Gorden, P. J. et al. Efficacy of vaccination with a *Klebsiella pneumoniae* siderophore receptor protein vaccine for reduction of *Klebsiella mastitis* in lactating cattle. *J Dairy Sci* 101, 10398-10408, doi:10.3168/jds.2017-14267 (2018).

29 Holt, K. E. et al. Genomic analysis of diversity, population structure, virulence, and antimicrobial resistance in *Klebsiella pneumoniae*, an urgent threat to public health. *Proc Natl Acad Sci USA* 112, E3574-3581, doi:10.1073/ pnas.1501049112 (2015).

30 Wang, J. et al. Nucleotide sequences of 16 transmissible plasmids identified in nine multidrug-resistant *Escherichia coli* isolates expressing an ESBL phenotype isolated from food-producing animals and healthy humans. *J Antimicrob Chemother* 69, 2658-2668, doi:10.1093/jac/ dku206 (2014).

31 Lawlor, M. S., O'Connor, C. & Miller, V. L. Yersiniabactin is a virulence factor for *Klebsiella pneumoniae* during pulmonary infection. *Infect Immun* 75, 1463-1472, doi:10.1128/IAI.00372-06 (2007).

32 Tomas, A. et al. Functional Genomic Screen Identifies *Klebsiella pneumoniae* Factors Implicated in Blocking Nuclear Factor kappaB (NF-kappaB) Signaling. *J Biol Chem* 290, 16678-16697, doi:10.1074/jbc.M114.621292 (2015).

33 Prody, C. A. & Neilands, J. B. Genetic and biochemical characterization of the *Escherichia coli* K-12 fhuB mutation. *J Bacteriol* 157, 874-880 (1984).

34 Kurupati, P., Teh, B. K., Kumarasinghe, G. & Poh, C. L. Identification of vaccine candidate antigens of an ESBL producing *Klebsiella pneumoniae* clinical strain by immunoproteome analysis. *Proteomics* 6, 836-844, doi: 10.1002/pmic.200500214 (2006).

35 Ferguson, A. D., Hofmann, E., Coulton, J. W., Diederichs, K. & Welte, W. Siderophore-mediated iron transport: crystal structure of FhuA with bound lipopolysaccharide. *Science* 282, 2215-2220, doi:10.1126/science.282.5397.2215 (1998).

36 Arunmanee, W. et al. Gram-negative trimeric porins have specific LPS binding sites that are essential for porin biogenesis. *Proc Natl Acad Sci USA* 113, E5034-5043, doi:10.1073/pnas.1602382113 (2016).

37 Cariss, S. J., Tayler, A. E. & Avison, M. B. Defining the growth conditions and promoter-proximal DNA sequences required for activation of gene expression by CreBC in *Escherichia coli*. *J Bacteriol* 190, 3930-3939, doi:10.1128/JB.00108-08 (2008).

38 Godoy, M. S., Nikel, P. I., Cabrera Gomez, J. G. & Pettinari, M. J. The CreC Regulator of *Escherichia coli*, a New Target for Metabolic Manipulations. *Appl Environ Microbiol* 82, 244-254, doi:10.1128/AEM.02984-15 (2016).

39 Tones, A. G., Vazquez-Juarez, R. C., Tutt, C. B. & Garcia-Gallegos, J. G. Pathoadaptive mutation that mediates adherence of shiga toxin-producing *Escherichia coli* O111. *Infect Immun* 73, 4766-4776, doi:10.1128/IAI.73.8.4766-4776.2005 (2005).

40 Tones, A. G., Jeter, C., Langley, W. & Matthysse, A. G. Differential binding of *Escherichia coli* O157:H7 to alfalfa, human epithelial cells, and plastic is mediated by a variety of surface structures. *Appl Environ Microbiol* 71, 8008-8015, doi:10.1128/AEM.71.12.8008-8015.2005 (2005).

41 Bin, L. I. & Ma, S. H. A. Successful High Density *Escherichia coli* Fermentation Using the Eppendorf Bio-Flo® 320 Advanced Bioprocess Control System. *BioProcessing Journal* 14, 20-24, doi:10.12665/J141.LiSha (2015).

42 Kroupitski, Y. et al. Identification of *Salmonella enterica* genes with a role in persistence on lettuce leaves during cold storage by recombinase-based in vivo expression technology. *Phytopathology* 103, 362-372, doi:10.1094/PHYTO-10-12-0254-FI (2013).

While the disclosure has been described through specific embodiments, routine modifications will be apparent to those skilled in the art and such modifications are intended to be within the scope of the present disclosure.

What is claimed is:

1. A method comprising administering to a female bovine animal in need thereof a composition comprising a protein comprising the amino acid sequence of SEQ ID NO:2, the protein optionally comprising a purification tag, and wherein the composition reduces an amount of bacteria in the female bovine animal, and wherein the composition is free of free from *Klebsiella* proteins other than SEQ ID NO:2 and wherein administration of the protein results in at least one of: i) increased milk production relative to milk production by female bovine animals vaccinated with a composition comprising a *Klebsiella pneumoniae* bacterial extract; ii) reduced severity of mastitis relative to severity of mastitis in female bovine animals vaccinated with a composition comprising a *Klebsiella pneumoniae* bacterial extract; or a combination of i) or ii).

2. The method of claim 1, wherein the composition comprises an adjuvant.

3. The method of claim 2, wherein the female bovine animal is in need of prophylaxis or treatment of a condition associated with the presence of Gram negative pathogenic bacteria, and wherein the composition reduces the amount of the Gram negative bacteria in the female bovine animal.

4. The method of claim 3, wherein the Gram negative pathogenic bacteria comprise *Klebsiella, E. coli, Salmonella*, or a combination thereof.

5. The method of claim 4, wherein the condition is associated with the *Klebsiella* or the *E. coli*, or a combination thereof.

6. The method of claim 4, wherein the condition comprises the mastitis.

7. The method of claim 6, wherein the administration inhibits the development or reduces the severity of the mastitis.

8. The method of claim 7, wherein the mastitis is associated with the presence of the *E. coli*.

9. The method of claim 8, wherein reducing the severity of the mastitis occurs and the likelihood that the mastitis will result in lethality is reduced.

10. The method of claim 6, wherein the condition comprises the metritis, and wherein the administration inhibits the development or reduces the severity of the metritis.

11. The method of claim 10, wherein the metritis is associated with the presence of the *Klebsiella* or the *E. coli*, or a combination thereof.

12. The method of claim 4, wherein the administering the composition improves the likelihood of a first service conception.

13. The method of claim 8, wherein the female bovine mammal is a primaparous or multiparous bovine animal.

14. The method of claim 4, wherein the administering improves the milk production by the female bovine mammal.

* * * * *

SEQUENCE LISTING

```
<160> NUMBER OF SEQ ID NOS: 4

<210> SEQ ID NO 1
<211> LENGTH: 1227
<212> TYPE: DNA
<213> ORGANISM: Klebsiella spp

<400> SEQUENCE: 1
atgaaacaag tcacttttgc tccccgtcat caccagctta ccaatattaa tacctggact      60
cccgacagcc agtggctggt attcgacgtt cgtccgtccg gcgcatcgtt taccggcgaa     120
accattgagc gagtgaacgt aaacagcggt actgtggaga ccatttatcg tgccacgcag     180
ggcgcgcacg tgggcgtggt aaccgtgcat ccaacccagg agcgctatgt gtttattcat     240 ggcccccgagc ggccggatgc gcagtggcag tatgattttc atcatcgccg cggggtggtg     300
gcctttcagg gggctgtcga gaatctggac gccatggaca ttaccccccc ctacacgccc     360
ggcgcgctgc gcggcggcag ccacgtccat gtctatagcc ccaacggtca gtttgtcagt     420
tttacctaca acgatcacgt gctgcaccag cgcgatccgg cgctggatct gcgcaacgtc     480
ggcgtggcgg cgccctatgg accggtgacg ccgcagggac agcatccgcg cgaatatggc     540
ggcagccact ggtgtgtgct ggtaagccgc acgacgccgc cacccgcgcc gggcagcgat     600
gagattaatc gcgcctatga ggagggctgg gtcgggaacc atactctggc gtttattggc     660
gatacgctgg cggaaaatgg cgataaagtg cctgagctgt ttattgtcga tctgccgcag     720
gatgaagccg gctggaagca gcctggcggg gcgccgctgg ccggtaccgc aaccacaatg     780
ccggcgccgc cggcgggcgt cagccagcgt cgtttgacct tcacccacca tcgccgctac     840
ccgggactgg tgaacgtccc gcgccactgg gtgcgcgcca atcccaggc gacggcgata     900 gccttttctga tgcgcgacga cgccggcgta gtgcagctgt ggcttatttc cccgcagggg     960
ggcgagccgc ggcagttgac gcatcacgcg tcgggtatcc agtcggcgtt taactggcat    1020
ccgtcgggag agtggctggg tttttgcgctg gaggatcgga ttgcctgctg ccatgccggt    1080
acgggagata tcaccttttt aaccgatacg catgcgcatg cgccctcggc ggacgcgatc    1140
gtcttttcgc cagacggtaa acagattgcc tggatggagg aggtggacgg ttatcgtcag    1200
ctgtgggtta cgcagaccgg acgataa                                        1227

<210> SEQ ID NO 2
<211> LENGTH: 408
<212> TYPE: PRT
<213> ORGANISM: Klebsiella spp

<400> SEQUENCE: 2

Met Lys Gln Val Thr Phe Ala Pro Arg His His Gln Leu Thr Asn Ile
1               5                   10                  15
```

```
Asn Thr Trp Thr Pro Asp Ser Gln Trp Leu Val Phe Asp Val Arg Pro
             20                  25                  30

Ser Gly Ala Ser Phe Thr Gly Glu Thr Ile Glu Arg Val Asn Val Asn
         35                  40                  45

Ser Gly Thr Val Glu Thr Ile Tyr Arg Ala Thr Gln Gly Ala His Val
     50                  55                  60

Gly Val Val Thr Val His Pro Thr Gln Glu Arg Tyr Val Phe Ile His
 65                  70                  75                  80

Gly Pro Glu Arg Pro Asp Ala Gln Trp Gln Tyr Asp Phe His His Arg
                 85                  90                  95

Arg Gly Val Val Ala Phe Gln Gly Ala Val Glu Asn Leu Asp Ala Met
                100                 105                 110

Asp Ile Thr Pro Pro Tyr Thr Pro Gly Ala Leu Arg Gly Gly Ser His
             115                 120                 125

Val His Val Tyr Ser Pro Asn Gly Gln Phe Val Ser Phe Thr Tyr Asn
130                 135                 140

Asp His Val Leu His Gln Arg Asp Pro Ala Leu Asp Leu Arg Asn Val
145                 150                 155                 160

Gly Val Ala Ala Pro Tyr Gly Pro Val Thr Pro Gln Gly Gln His Pro
                165                 170                 175

Arg Glu Tyr Gly Gly Ser His Trp Cys Val Leu Val Ser Arg Thr Thr
                180                 185                 190

Pro Ala Pro Ala Pro Gly Ser Asp Glu Ile Asn Arg Ala Tyr Glu Glu
            195                 200                 205

Gly Trp Val Gly Asn His Thr Leu Ala Phe Ile Gly Asp Thr Leu Ala
            210                 215                 220

Glu Asn Gly Asp Lys Val Pro Glu Leu Phe Ile Val Asp Leu Pro Gln
225                 230                 235                 240

Asp Glu Ala Gly Trp Lys Gln Pro Gly Gly Ala Pro Leu Ala Gly Thr
                245                 250                 255

Ala Thr Thr Met Pro Ala Pro Pro Ala Gly Val Ser Gln Arg Arg Leu
            260                 265                 270

Thr Phe Thr His His Arg Arg Tyr Pro Gly Leu Val Asn Val Pro Arg
            275                 280                 285

His Trp Val Arg Ala Asn Pro Gln Ala Thr Ala Ile Ala Phe Leu Met
290                 295                 300

Arg Asp Asp Ala Gly Val Val Gln Leu Trp Leu Ile Ser Pro Gln Gly
305                 310                 315                 320

Gly Glu Pro Arg Gln Leu Thr His His Ala Ser Gly Ile Gln Ser Ala
                325                 330                 335

Phe Asn Trp His Pro Ser Gly Leu Trp Leu Gly Phe Ala Leu Glu Asp
            340                 345                 350

Arg Ile Ala Cys Cys His Ala Gly Thr Gly Asp Ile Thr Phe Leu Thr
            355                 360                 365

Asp Thr His Ala His Ala Pro Ser Ala Asp Ala Ile Val Phe Ser Pro
            370                 375                 380

Asp Gly Lys Gln Ile Ala Trp Met Glu Glu Val Asp Gly Tyr Arg Gln
385                 390                 395                 400

Leu Trp Val Thr Gln Thr Gly Arg
                405

<210> SEQ ID NO 3
<211> LENGTH: 415
```

```
<212> TYPE: PRT
<213> ORGANISM: E. coli O157:H7

<400> SEQUENCE: 3

Met Ala Gly Pro Val Leu Tyr Gln Asp Arg Ala Met Lys Gln Ile Thr
1               5                   10                  15

Phe Ala Pro Arg Asn His Leu Leu Thr Asn Thr Asn Thr Trp Thr Pro
                20                  25                  30

Asp Ser Gln Trp Leu Val Phe Asp Val Arg Pro Ser Gly Ala Ser Phe
            35                  40                  45

Thr Gly Glu Thr Ile Glu Arg Val Asn Ile His Thr Gly Glu Val Glu
        50                  55                  60

Val Ile Tyr Arg Ala Ser Gln Gly Ala His Val Gly Val Val Thr Val
65                  70                  75                  80

His Pro Lys Ser Glu Lys Tyr Val Phe Ile His Gly Pro Glu Asn Pro
                85                  90                  95

Asp Glu Thr Trp His Tyr Asp Phe His His Arg Arg Gly Val Ile Val
            100                 105                 110

Glu Gly Gly Lys Met Ser Asn Leu Asp Ala Met Asp Ile Thr Ala Pro
        115                 120                 125

Tyr Thr Pro Gly Val Leu Arg Gly Gly Ser His Val His Val Phe Ser
130                 135                 140

Pro Asn Gly Glu Arg Val Ser Phe Thr Tyr Asn Asp His Val Met His
145                 150                 155                 160

Glu Leu Asp Pro Ala Leu Asp Leu Arg Asn Val Gly Val Ala Ala Pro
                165                 170                 175

Phe Gly Pro Val Asn Val Gln Lys Gln His Pro Arg Glu Tyr Ser Gly
            180                 185                 190

Ser His Trp Cys Val Leu Val Ser Lys Thr Thr Pro Thr Pro Gln Pro
        195                 200                 205

Gly Ser Asp Glu Ile Asn Arg Ala Tyr Glu Glu Gly Trp Val Gly Asn
210                 215                 220

His Ala Leu Ala Phe Ile Gly Asp Thr Leu Ser Pro Lys Gly Glu Lys
225                 230                 235                 240

Val Pro Glu Leu Phe Ile Val Glu Leu Pro Gln Asp Glu Ala Gly Trp
                245                 250                 255

Lys Ala Ala Gly Asp Ala Pro Leu Ser Gly Thr Glu Thr Thr Leu Pro
            260                 265                 270

Ala Pro Pro Arg Gly Val Val Gln Arg Arg Leu Thr Phe Thr His His
        275                 280                 285

Arg Ala Tyr Pro Gly Leu Val Asn Val Pro Arg His Trp Val Arg Cys
290                 295                 300

Asn Pro Gln Gly Thr Gln Ile Ala Phe Leu Met Arg Asp Asp Asn Gly
305                 310                 315                 320

Ile Val Gln Leu Trp Leu Ile Ser Pro Gln Gly Gly Glu Pro Arg Gln
                325                 330                 335

Leu Thr His Asn Lys Thr Asp Ile Gln Ser Ala Phe Asn Trp His Pro
            340                 345                 350

Ser Gly Glu Trp Leu Gly Phe Val Leu Asp Asn Arg Ile Ala Cys Ala
        355                 360                 365

His Ala Gln Ser Gly Glu Val Glu Tyr Leu Thr Glu His His Ala Asn
370                 375                 380

Ser Pro Ser Ala Asp Ala Val Val Phe Ser Pro Asp Gly Gln Trp Leu
385                 390                 395                 400
```

-continued

```
Ala Trp Met Glu Gly Gly Gln Leu Trp Ile Thr Glu Thr Asp Arg
                405                 410                 415

<210> SEQ ID NO 4
<211> LENGTH: 408
<212> TYPE: PRT
<213> ORGANISM: Salmonella enterica

<400> SEQUENCE: 4

Met Lys Gln Ile Thr Phe Thr Pro Arg His His Gln Leu Thr Asn Thr
1               5                   10                  15

Asn Thr Trp Thr Pro Asp Ser Gln Trp Leu Val Phe Asp Val Arg Pro
            20                  25                  30

Ser Gly Ala Ser Phe Thr Gly Lys Thr Ile Glu Arg Val Asn Val His
        35                  40                  45

Thr Gly Asp Val Glu Val Ile Tyr Arg Ala Val Gln Gly Ala His Val
    50                  55                  60

Gly Val Val Thr Val His Pro Ala Asp Asn His Tyr Val Phe Ile His
65                  70                  75                  80

Gly Pro Glu Asn Pro Asp Glu Thr Trp His Tyr Asp Phe His His Arg
                85                  90                  95

Arg Gly Val Ile Ala Thr Pro Gly Gly Val Thr Asn Leu Asp Ala Met
            100                 105                 110

Asp Ile Thr Ala Pro Tyr Thr Pro Gly Ala Leu Arg Gly Gly Ser His
        115                 120                 125

Val His Val Phe Ser Pro Asn Gly Glu Leu Val Ser Phe Thr Tyr Asn
    130                 135                 140

Asp His Val Leu His Glu Arg Asp Pro Ala Leu Asp Leu Arg Asn Val
145                 150                 155                 160

Gly Val Ala Ala Pro Tyr Gly Pro Val Thr Val Pro Val Gln His Pro
                165                 170                 175

Arg Glu Tyr Ser Gly Ser His Trp Cys Val Leu Val Ser Arg Thr Thr
            180                 185                 190

Pro Ala Pro Arg Pro Gly Ser Asp Asp Ile Asn Arg Ala Tyr Glu Glu
        195                 200                 205

Gly Trp Val Gly Asn Arg Gln Ile Ala Phe Ile Gly Asp Thr Leu Ser
    210                 215                 220

Leu Thr Gly Gln Lys Val Pro Glu Leu Phe Ile Val Asp Leu Pro Cys
225                 230                 235                 240

His Glu Asn Gly Trp Lys Gln Ala Gly Asp Thr Pro Leu Thr Gly Thr
                245                 250                 255

Glu Ser Thr Met Pro Ser Pro Pro Leu Gly Val Val Gln Arg Arg Leu
            260                 265                 270

Thr Phe Thr His Gln Arg Val Tyr Pro Gly Leu Thr Asn Glu Pro Arg
        275                 280                 285

His Trp Val Arg Ser Asn Pro Gln Ala Thr Ala Ile Ala Phe Leu Met
    290                 295                 300

Arg Asp Asp Asn Gly Val Ala Gln Leu Trp Leu Ile Ser Pro Gln Gly
305                 310                 315                 320

Gly Glu Pro Arg Gln Leu Thr His His Ala Thr Gly Val Gln Ser Ala
                325                 330                 335

Phe Asn Trp His Pro Ser Gly Lys Trp Leu Gly Leu Val Leu Glu Asn
            340                 345                 350

Arg Ile Ala Cys Cys Asp Ala Gln Ser Gly Arg Ile Asp Phe Leu Thr
```

-continued

```
            355                 360                 365
Ala Arg His Asp Asn Pro Pro Ser Ala Asp Ala Val Val Phe Ser Pro
        370                 375                 380

Asp Gly Arg His Val Ala Trp Met Glu Glu Val Lys Gly Phe Arg Gln
385                 390                 395                 400

Leu Trp Val Thr Glu Thr Gly Arg
                405
```